(12) United States Patent
An et al.

(10) Patent No.: US 11,119,341 B2
(45) Date of Patent: Sep. 14, 2021

(54) CONTACT LENS HAVING ENERGY HARVESTING PART

(71) Applicant: Samsung Electronics Co., Ltd., Suwon-si (KR)

(72) Inventors: Kwang-dek An, Hwaseong-si (KR); Jun-ho Koh, Suwon-si (KR); Bo-seok Moon, Gunpo-si (KR); Jae-hyun Park, Seoul (KR); Young-eun Lee, Seoul (KR); Ji-yeon Han, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/578,975

(22) PCT Filed: Jan. 25, 2016

(86) PCT No.: PCT/KR2016/000754
§ 371 (c)(1),
(2) Date: Dec. 1, 2017

(87) PCT Pub. No.: WO2016/195201
PCT Pub. Date: Dec. 8, 2016

(65) Prior Publication Data
US 2018/0136492 A1 May 17, 2018

(30) Foreign Application Priority Data
Jun. 1, 2015 (KR) .................. 10-2015-0077485

(51) Int. Cl.
*G02C 11/00* (2006.01)
*G02C 7/04* (2006.01)
(Continued)

(52) U.S. Cl.
CPC ............ *G02C 11/10* (2013.01); *A61B 5/1103* (2013.01); *A61B 5/145* (2013.01); *A61B 5/1486* (2013.01);
(Continued)

(58) Field of Classification Search
CPC ... G02C 11/10; H01L 41/113; H01L 41/0471; H02N 2/18; A61B 5/1103; A61B 5/145;
(Continued)

(56) References Cited

U.S. PATENT DOCUMENTS 5,217,015 A * 6/1993 Kaye ................. A61B 3/16
600/398
8,764,185 B1 * 7/2014 Biederman ............. G02C 7/04
351/159.02
(Continued)

FOREIGN PATENT DOCUMENTS

| CN | 203054364 U | 7/2013 |
| CN | 103329030 A | 9/2013 |

(Continued)

OTHER PUBLICATIONS

European Search Report dated Apr. 4, 2018, issued in European Application No. 16803556.6-1132.
(Continued)

*Primary Examiner* — Travis S Fissel
(74) *Attorney, Agent, or Firm* — Jefferson IP Law, LLP

(57) ABSTRACT

A contact lens including an energy harvesting unit is provided. The contact lens includes a sensor that detects biometric information of a user, and a power that transforms a dynamic energy generated by a movement of an eye part of the user into electrical energy and provides the sensor with the electrical energy.

18 Claims, 51 Drawing Sheets

(51) Int. Cl.
  *H02N 2/18* (2006.01)
  *H01L 41/047* (2006.01)
  *A61B 5/145* (2006.01)
  *A61B 5/00* (2006.01)
  *A61B 5/11* (2006.01)
  *H01L 41/113* (2006.01)
  *A61B 5/1486* (2006.01)

(52) U.S. Cl.
  CPC ...... *A61B 5/14507* (2013.01); *A61B 5/14532* (2013.01); *A61B 5/6821* (2013.01); *G02C 7/04* (2013.01); *H01L 41/113* (2013.01); *H02N 2/18* (2013.01); *A61B 2560/0214* (2013.01); *H01L 41/0471* (2013.01)

(58) Field of Classification Search
  CPC ............ A61B 5/14507; A61B 5/14532; A61B 5/1486; A61B 5/6821; A61B 2560/0214
  USPC ........................................ 351/159.02, 159.03
  See application file for complete search history.

(56) References Cited

U.S. PATENT DOCUMENTS

| | | | |
|---|---|---|---|
| 9,500,884 B2 | 11/2016 | Egan et al. | |
| 9,864,213 B2 | 1/2018 | Otts et al. | |
| 10,025,118 B1 | 7/2018 | Markus et al. | |
| 2004/0027536 A1* | 2/2004 | Blum | B29D 11/00826 351/159.03 |
| 2005/0099594 A1 | 5/2005 | Blum et al. | |
| 2008/0208335 A1 | 8/2008 | Blum et al. | |
| 2010/0103368 A1 | 4/2010 | Amirparviz et al. | |
| 2011/0224656 A1* | 9/2011 | Anderson | A61N 5/06 606/3 |
| 2012/0140167 A1* | 6/2012 | Blum | A61F 2/1624 351/159.34 |
| 2012/0268712 A1* | 10/2012 | Egan | G02C 7/085 351/159.34 |
| 2014/0192311 A1* | 7/2014 | Pletcher | H01L 31/0445 351/158 |
| 2014/0192318 A1* | 7/2014 | Guth | A61B 3/09 351/205 |
| 2014/0206966 A1 | 7/2014 | Liu et al. | |

FOREIGN PATENT DOCUMENTS

| | | |
|---|---|---|
| CN | 104204914 A | 12/2014 |
| CN | 103329030 B | 9/2015 |
| EP | 2647336 A1 | 10/2013 |
| JP | 2014204468 A2 * | 10/2014 |
| KR | 10-2011-0073530 A | 6/2011 |
| KR | 10-2011-0094675 A | 8/2011 |
| KR | 10-2013-0116878 A | 10/2013 |
| WO | 2013/112862 A1 | 8/2013 |
| WO | 2014/209479 A1 | 12/2014 |
| WO | 2015/035357 A1 | 3/2015 |

OTHER PUBLICATIONS

International Search Report dated Apr. 21, 2016, issued in International Application No. PCT/KR2016/000754.
Chinese Office Action dated Nov. 20, 2018, issued in the Chinese Patent Application No. 201680032391.2.
Chinese Office Action dated Jul. 2, 2019, issued in the Chinese Patent Application No. 201680032391.2.
Korean Office Action dated Aug. 12, 2020, issued in Korean Patent Application No. 10-2015-0077485.

* cited by examiner

CONTACT LENS HAVING ENERGY HARVESTING PART

TECHNICAL FIELD

The present disclosure relates to a contact lens that is directly worn on the eye of a user, and more particularly, to a contact lens including an energy harvesting unit.

BACKGROUND ART

Research into continuously monitoring a bio status of a user by including a sensor in a contact lens directly worn on the eye of the user has been proposed. For example, research into determining whether a contact lens wearer has diabetes and the progress degree of diabetes by including, in the contact lens, a biosensor for detecting a blood sugar change and thus stably collecting and analyzing tear even when just wearing a contact lens is being conducted.

When a sensor is included in a contact lens as described above, electrical energy for driving the sensor needs to be provided to the contact lens. Thus, a method of supplying electrical energy to a contact lens via micro solar cells or wireless charging, or separating radio frequency (RF) electrical energy from RF electromagnetic waves supplied during communication via an RF transceiver attached to a body part of a user other than the eyes of the user and utilizing the RF electrical energy as operational power, or receiving operational power of a sensor by including a thin film battery is being proposed.

DETAILED DESCRIPTION OF THE INVENTION

Technical Problem

In a method of supplying electrical energy to a contact lens via micro solar cells, charging efficiency rapidly decreases at places where sunlight is weak. A wireless charging method is not free of harmfulness controversy due to electromagnetic wave exposure. A thin film battery provides low energy storage efficiency. Thus, the present disclosure provides a method of providing electrical energy to a sensor of a contact lens while addressing these problems.

Technical Solution

According to an aspect of the present invention, there is provided a contact lens including a lens portion placed on an eye of a user, a sensor configured to detect biometric information of the user, and a power configured to transform a dynamic movement generated by a movement of the eye part into electrical energy and provide the sensor with the electrical energy.

The lens portion may have a concave surface and a convex surface, and the concave surface may contact a cornea surface of the eye.

When an electrical energy amount harvested by the power is equal to or greater than a sensing-enabling power amount, the sensor may be driven to detect information of the user.

The contact lens may further include a signal processor configured to process a signal detected by the sensor, a communicator configured to transmit information detected by the sensor to an external device, and a controller configured to control the sensor, the signal processor, and the communicator. When an electrical energy amount harvested by the power is equal to or greater than a communication-enabling power amount, the controller may drive the communicator to attempt to connect to the external device. When a number of eye blinks of the user is equal to or greater than a reference number, the controller may drive the communicator to attempt to connect to the external device.

The biometric information detected by the sensor may be at least one of a blood sugar concentration of the user, blinking, the number of eye blinks of the user, a duration of eye-closing of the user, a pattern of blinking of the user, an eyeball movement of the user, a temperature of the user, a pulse of the user, and information about a biomaterial included in tear of the user.

The contact lens may further include a display configured to output information detected by the sensor or information received from an external electronic device.

The contact lens may further include a memory configured to store the information detected by the sensor or the information received from the external electronic device. The memory may be non-volatile memory.

The power may include an energy harvesting unit that harvest a dynamic movement generated by a movement of at least one of the eye and the eyelid of the user as electrical energy.

The energy harvesting unit may include a first piezoelectric element, the first piezoelectric element including a first piezoelectric layer that is bent due to the movement of at least one of the eye and the eyelid of the user, and first and second electrodes that contact the first piezoelectric layer and collect electrical energy generated due to deformation of the first piezoelectric layer.

For example, the first and second electrodes may be arranged apart from each other on a first surface of the first piezoelectric layer. In this case, the first and second electrodes may face each other, and may be arranged such as to elongate toward each other at a plurality of spots and alternate with each other.

As another example, the first and second electrodes may be respectively arranged on a first surface of the first piezoelectric layer and a second surface of the first piezoelectric layer opposite to the first surface. In this case, at least one of the first and second electrodes may be formed in a lattice pattern, a zigzag pattern, or a comb electrode pattern. For example, when the first and second electrodes have comb electrode patterns, the first electrode may extend long in a first direction at a plurality of spots on the first surface of the first piezoelectric layer, and the second electrode may extend long in a second direction at a plurality of spots on the second surface of the first piezoelectric layer. The first direction and the second direction may be the same or may be different.

The energy harvesting unit may further include a second piezoelectric element, the second piezoelectric element comprising a second piezoelectric layer and third and fourth electrodes that contact the second piezoelectric layer and collect electricity generated due to deformation of the second piezoelectric layer. The first and second piezoelectric elements may have a stacked structure. One of the third and fourth electrodes may be common to one of the first and second electrodes.

The contact lens may include a circuit layer equipped with the sensor, and a piezoelectric element layer equipped with the first piezoelectric element. In other words, a layer equipped with the sensor, and a layer equipped with the first piezoelectric element may be different from each other. The piezoelectric element layer may be stacked to be positioned farther from a surface of the lens portion that directly contacts the eye of the user; than the circuit layer is. In other words, the piezoelectric element layer may be stacked to be positioned outside when the contact lens is worn on the eye of the user. The contact lens may further include a spacer positioned between the circuit layer and the piezoelectric element layer or between the circuit layer and the lens portion. The spacer may minimize transmission of an external force due to a movement of the eye or eyelid of the user to the circuit layer so that the piezoelectric element layer may be more effectively bent. The spacer may be an air layer, a liquid layer, or a soft material layer that is very flexible.

The sensor and the first piezoelectric element may be provided on the same layer. For example, the first piezoelectric layer may be provided on a center region of the lens portion, and the sensor may be provided on an outer region of the lens portion.

The power may further include a power storage and a rectifying circuit. The power storage may include a capacitor, such as an ultra-small super capacitor. This capacitor may be provided on an outer circumference of the lens portion. Alternatively, this capacitor may be provided on one region of the outer circumference of the lens portion.

The sensor may include at least one of a bio sensor, a light-detection sensor, a gyro sensor, and an inertia sensor. The bio sensor may be, for example, a blood sugar detection sensor.

The sensor may detect a movement of the eye of the user. For example, the sensor may include a gyro sensor and an inertia sensor to detect a movement of the eye of the user.

The sensor may detect blinking of the user. For example, when the energy harvesting unit is a piezoelectric type, the sensor may count the number of eye blinks from a waveform of power generated according to a movement of the eyelid. Alternatively, the sensor may include a light-detection sensor to count blockage of external light according to blinking and thus count the number of eye blinks.

According to another aspect of the present invention, there is provided a contact lens including a lens portion placed on an eye of a user; a sensor configured to detect biometric information of the user; and a power configured to transform biochemical energy into electrical energy via a reaction of tear of the eye part with an electrode and provide the sensor with the electrical energy.

The power may include a collector that collects the tear of the eye part; and the electrode provided on at least a partial region of the collector, and may transform the biochemical energy into the electrical energy via a reaction of tear collected by the collector with the electrode. The power may be understood as a biofuel cell that uses the tear of the eye part.

The collector may include a micro tear-tube of which one end is exposed to the outside of the lens portion, and a microtube connected to the micro tear-tube and equipped with the electrode.

The microtube may be ring-shaped, and the micro tear-tube may extend in a diameter direction from an edge of the lens portion to the microtube.

According to another aspect of the present invention, there is provided an electronic device including a communicator configured to communicate with a contact lens; and a controller configured to process information received from the contact lens.

For example, the information received by the electronic device from the contact lens may be information about a movement of an eye of a user, and the controller may extract at least one of a direction of the movement of the eye of the user and a degree of the movement, based on the information about the movement of the eye of the user, and generate a first control command corresponding to the at least one of the direction of the movement of the eye of the user and the degree of the movement. The first control command may be a control command for the electronic device or a control command for another electronic device.

As another example, the information received by the electronic device from the contact lens may be information about blinking of the user, and the controller may extract at least one of the number of eye blinks per unit time and a duration of an eye blink, based on the information about the blinking of the user, and generate a second control command corresponding to the at least one of the number of eye blinks per unit time and the duration of an eye blink. The second control command may be a control command for the electronic device in communication with the contact lens or a control command for another electronic device.

As another example, the information received by the electronic device from the contact lens may be the information about the blinking of the user, and the controller may detect a fatigue degree of the user, based on the information about the blinking of the user, and may generate a third control command when the fatigue degree of the user exceeds a reference value. The third control command may be a control command of generating an alarm that warns the user.

As another example, the information received by the electronic device from the contact lens may be the information about a blinking pattern of the user, and the controller may generate a fourth control command, based on the information about the blinking pattern of the user. For example, the blinking pattern may be a combination of long eye-closing and short eye-closing, and long eye-closing and short eye-closing may be combined like a Morse code to thereby express a character or a sentence. When the electronic device receives the information about the blinking pattern of the user as described above, the electronic device may display a character or sentence corresponding to a blinking pattern of the user or may output the character or sentence via a speaker.

The electronic device may be a mobile telephone, a smartphone, a tablet computer, a personal digital assistant (PDA), a laptop computer, a personal computer (PC), a television (TV), a game player, a remote controller, or an automobile.

According to another aspect of the present invention, there is provided a method of driving a contact lens, the contact lens including a lens portion placed on an eye of a user; a sensor provided within the lens portion and configured to detect biometric information of the user; and a power configured to transform a dynamic movement generated by a movement of the eye part into electrical energy and provide the sensor with the electrical energy. The method includes the operations of harvesting electrical energy from the eye part of the user by using the power and driving the sensor by using the harvested electrical energy.

When the amount of the harvested electrical energy is equal to or greater than a sensing-enabling power amount, the sensor may be driven.

When the amount of the harvested electrical energy is equal to or greater than a communication-enabling power amount, a connection to an external device may be attempted.

When the number of eye blinks of the user is equal to or greater than a reference number, a connection to the external device may be attempted.

A method of driving a contact lens, according to an example, includes the operations of connecting an external device; determining whether to transmit stored data together with real-time data to the external device; and transmitting real-time data detected in real time by a sensor to the external device when the stored data is not transmitted together, and transmitting the stored data together with the real-time data to the external device when the stored data is transmitted together.

A method of driving a contact lens, according to another example, may include the operations of requesting an external device for a connection; transmitting data when a connection response is received from the external device; and resetting a memory when a reception-completion response is received from the external device.

A method of driving a contact lens, according to another example, may include the operations of responding to a connection requested by an external device; transmitting data when a data transmission command is received from the external device; and resetting a memory when a reception-completion response is received from the external device.

A method of driving a contact lens, according to another example, may include the operations of transmitting a power-on response when wireless power is received from an external device; transmitting data when a data transmission command is received from the external device; and resetting a memory when a reception-completion response is received from the external device.

A method of driving a contact lens, according to another example, may include the operations of attempting to connect a second contact lens to an external device; determining whether the first contact lens is connected to the external device, if the connection of the second contact lens to the external device is failed; and re-attempting the connection of the second contact lens to the external device after the laps of a preset time if the first contact lens is connected to the external device.

A method of driving a contact lens, according to another example, may include the operations of counting blinking; and driving a light-emitting device when the number of eye blinks reaches a preset value. A method of driving a contact lens, according to another example, includes the operations of counting blinking; and transmitting information about the number of eye blinks to an external electronic device when the number of eye blinks reaches a preset value.

A method of driving a contact lens, according to another example, includes the operations of detecting a pattern of blinking; and transmitting information about the pattern of the blinking to an external electronic device. For example, the operation of detecting the pattern of blinking may include distinguishing long eye-closing from short eye-closing according to a duration of eye-closing to detect the pattern of blinking.

A sensor of the first contact lens and a sensor of the second contact lens may detect the same type or different types. For example, the first contact lens may track an eye movement of a wearer, and the second contact lens may track blinking of the wearer.

Advantageous Effects

A contact lens according to a disclosed embodiment may produce electrical energy by including an energy harvesting unit.

Because the energy harvesting unit does not greatly increase a typical thickness of a contact lens, the energy harvesting unit may secure comfortable wearing of the user.

DESCRIPTION OF THE DRAWINGS

FIGS. 27A-7F are views for explaining a method of manufacturing a contact lens, according to an embodiment.

MODE OF THE INVENTION

Figure 1:
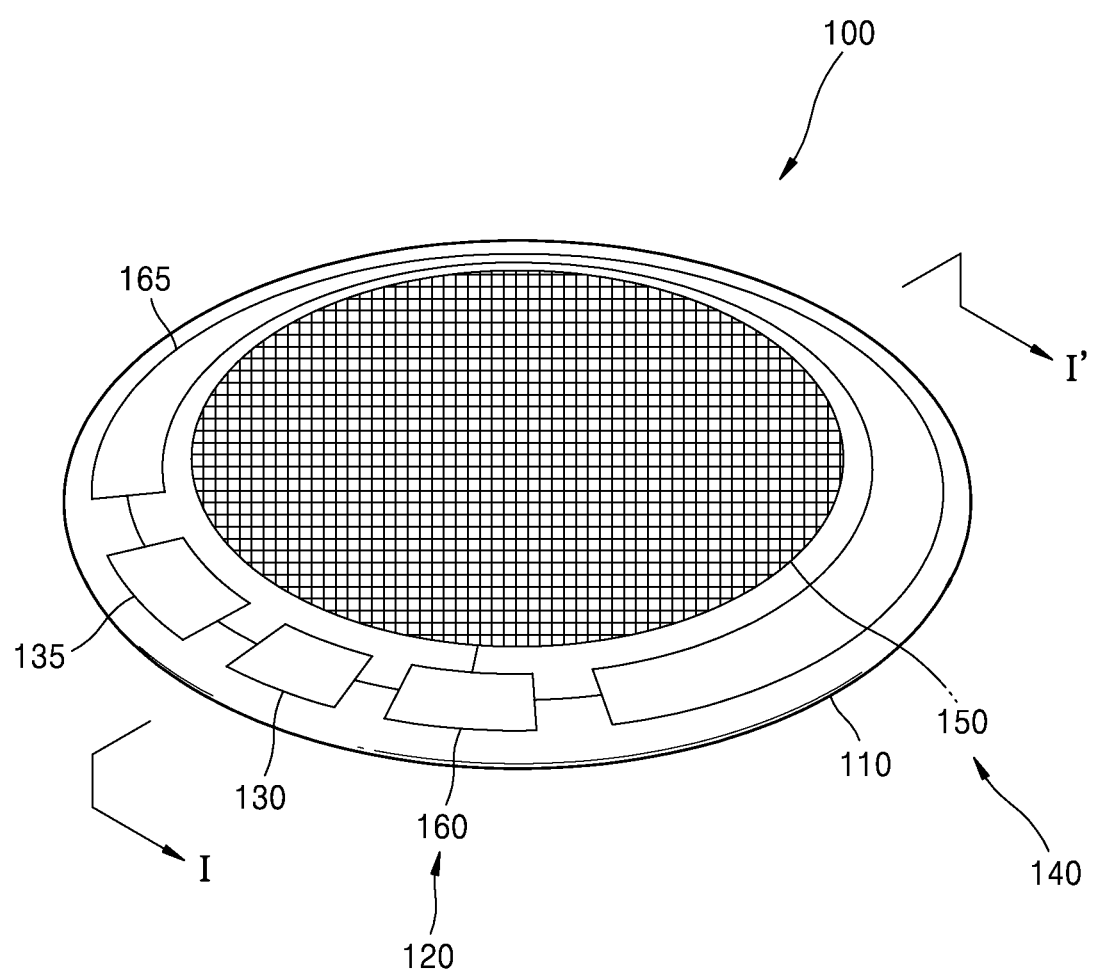
FIG. 1 is a schematic plan view of a contact lens according to an embodiment.

The attached drawings for illustrating exemplary embodiments are referred to in order to gain a sufficient understanding of the merits and features thereof, and methods for accomplishing the merits and features thereof. The invention may, however, be embodied in many different forms and should not be construed as being limited to the embodiments set forth herein; rather, these embodiments are provided so that this disclosure will be thorough and complete, and will fully convey the concept of the invention to those skilled in the art. The scope of the present invention is only defined by the appended claims. Like reference numerals in the drawings denote like elements, and, in the drawings, the sizes or thicknesses of elements may be exaggerated for clarity of explanation.

Terms used herein will be described briefly, and the present invention will be described in detail.

Although general terms widely used at present were selected for describing the present disclosure in consideration of the functions thereof, these general terms may vary according to intentions of one of ordinary skill in the art, case precedents, the advent of new technologies, or the like. Terms arbitrarily selected by the applicant of the present invention may also be used in a specific case. In this case, their meanings need to be given in the detailed description of the invention. Hence, the terms must be defined based on their meanings and the contents of the entire specification, not by simply stating the terms.

The terms "comprises" and/or "comprising" or "includes" and/or "including" when used in this specification, specify the presence of stated elements, but do not preclude the presence or addition of one or more other elements. In addition, terms such as " . . . unit", " . . . module", or the like refer to units that perform at least one function or operation, and the units may be implemented as hardware or software or as a combination of hardware and software.

The present invention will now be described more fully with reference to the accompanying drawings, in which exemplary embodiments of the invention are shown. In the drawings, elements irrelevant to the descriptions of the present invention are omitted to clearly explain the present invention.

Figure 2:
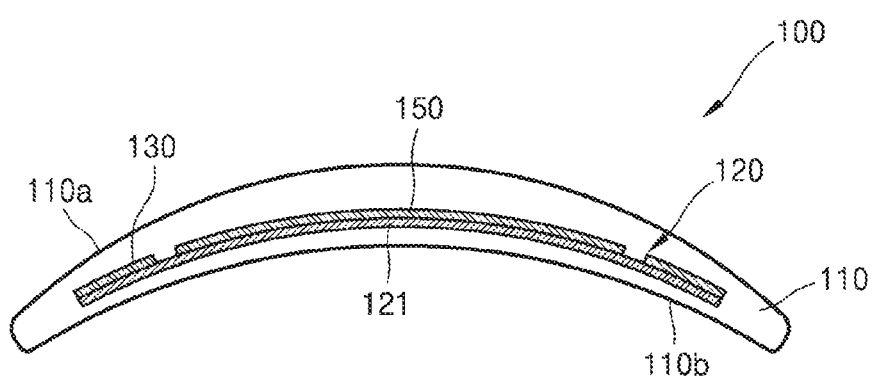
FIG. 2 is a sectional view of the contact lens taken along line I-I' of FIG. 1.

FIG. 1 is a schematic perspective view of a contact lens according to an embodiment, FIG. 2 is a sectional view of the contact lens taken along line of FIG. 1.

Referring to FIGS. 1 and 2, a contact lens 100 according to an embodiment includes a lens portion 110 placed directly on the eye of a user (wearer), and an electronic element unit 120 provided in the lens portion 110.

The lens portion 110 is a layer that performs refraction of the contact lens 100, and has a concave surface and a convex surface. The concave surface may contact the surface of the cornea of the eye. The lens portion 110 may have a well-known contact lens shape. The lens portion 110 may be formed of a material used to form a well-known contact lens. For example, soft lenses may be formed of soft polymer, and hard lenses may be formed of hard polymer.

The electronic element unit 120 includes a sensor 130, a display 135, and a power 140. The power 140 includes a piezoelectric element 150, a rectifying circuit 160, and a power storage 165. The electronic element unit 120 may be formed of a circuit thin film on a substrate 121 via a thin film manufacturing process. The substrate 121 may be formed of a transparent and flexible material. For example, the substrate 121 may be formed of a well-known high molecular substance material, such as polycarbonate (PC), polyester (PET), polyethylenenapthalate (PEN), or polyethersulfone (PES). The substrate 121 may have a disk shape. The piezoelectric element 150 from among circuit elements of the electronic element unit 120 may be arranged on a center of the substrate 121, and all elements except for the piezoelectric element 150 (i.e., the sensor 130, the display 135, the rectifying circuit 160, and the power storage 165) may be arranged around the piezoelectric element 150. According this layout, the piezoelectric element 150 may secure a wide area, and may suppress refraction or blockage of transmitted light by the sensor 130, the display 135, the rectifying circuit 160, and the power storage 165. The electronic element unit 120 may be formed of a transparent material, or may be fabricated very thinly so as to be formed transparently. For example, the electronic element unit 120 may be formed of a thin film having a thickness of several tens or several hundreds of μm. In some cases, there may be circuit elements having somewhat low transparency. These circuit elements having low transparency may secure transparency of the contact lens 100 by being arranged around the piezoelectric element 150 as described above.

The electronic element unit 120 may be positioned within the lens portion 110. In some cases, a portion of the electronic element unit 120 may be exposed via the lens portion 110. For example, when the sensor 130 of the electronic element unit 120 is a sensor for detecting a bio material from tear of the user, like a blood sugar detecting sensor, a detecting surface of the sensor is exposed via the lens portion 110.

The electronic element unit 120 may be manufactured separately from the lens portion 110 and may be inserted into the lens portion 110 when the lens portion 110 is formed. According to manufacturing methods, the lens portion 110 may be formed of an integrated polymer mould, or may be formed by bonding two layers with each other with the electronic element unit 120 interposed therebetween.

The lens portion 110 may be formed to have a curved surface having a predetermined refractive power. In some cases, the lens portion 110 may be designed not to have a refractive power. A method of manufacturing the lens portion 110 will be described in more detail later.

Figure 3:
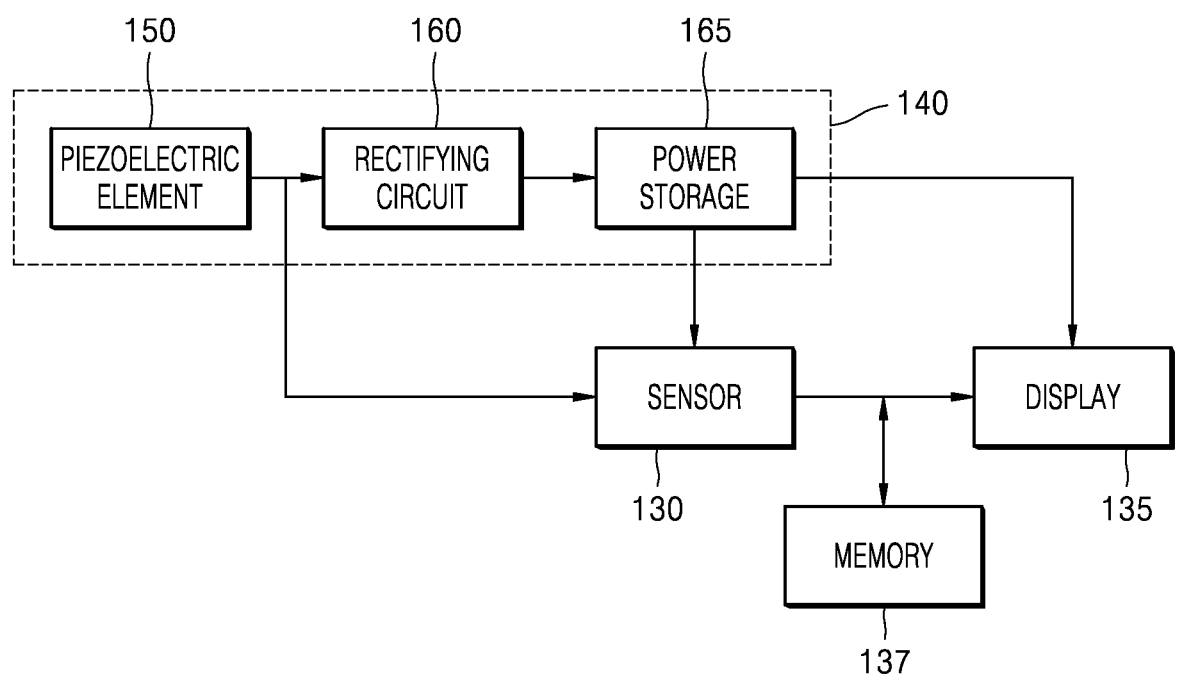
FIG. 3 is a schematic block diagram of a structure of an electronic element unit of the contact lens of FIG. 1.

FIG. 3 is a schematic block diagram of a structure of the electronic element unit 120.

Referring to FIG. 3, the sensor 130 detects biometric information of the user. As will be described later, because a voltage waveform issued by the piezoelectric element 150 of the power 140 may correspond to blinking of the user, the sensor 130 may detect blinking of the user from the voltage waveform issued by the piezoelectric element 150. Moreover, the sensor 130 may count blinking.

The display 135 may include a light-emitting device and a driving circuit of the light-emitting device. Depending on the type of a light-emitting device, a driving circuit may be omitted. The light-emitting device may be a light emitting diode (LED) or an organic light emitting diode (OLED). Light emitted from the light-emitting device is incident upon the pupil of the user while being reflected and diffused within the lens portion 110, and enables the user to recognize lighting of the light-emitting device. As will be described later, the light-emitting device of the display 135 lights up based on information of the user sensed by the sensor 130, thereby informing the user of predetermined information.

A memory 137 of FIG. 3 for storing the information of the user sensed by the sensor 130 may be additionally included. For example, the memory 137 may count an eye blink whenever the eye blink is detected by the sensor 130, and may store the number of eye blinks. The memory 137 may use non-volatile memory so that, even when no power is supplied, the stored information does not disappear. In some cases, a circuit of the sensor 130 or the display 135 may directly count the number of eye blinks. In this case, the memory may be omitted.

The power storage 165 may be a capacitor. For example, the power storage 165 may have a super capacitor structure having a design that maximizes facing areas of two electrodes. The storage capacity of the power storage 165 for storing electrical energy may increase in proportion to an area occupied by the power storage 165. Considering this point, the power storage 165 may be formed in a ring shape around the piezoelectric element 150, as shown in FIG. 1.

The piezoelectric element 150 is an example of an energy harvesting unit that transforms dynamical energy generated due to a movement of an eye part of the user into electrical energy, namely, harvests energy. The eye part indicates not only the eyeball itself but also at least one of the eyelid, the lacrimal drift, the tear on the surface of the eyeball, the extraocular muscle, and the like. The dynamical energy is energy determined according to a dynamic state and thus may be referred to as mechanical energy, and is formed by summing kinetic energy and potential energy of an object.

A mechanical energy conservation law is applied when there are no frictions.

Figure 4:
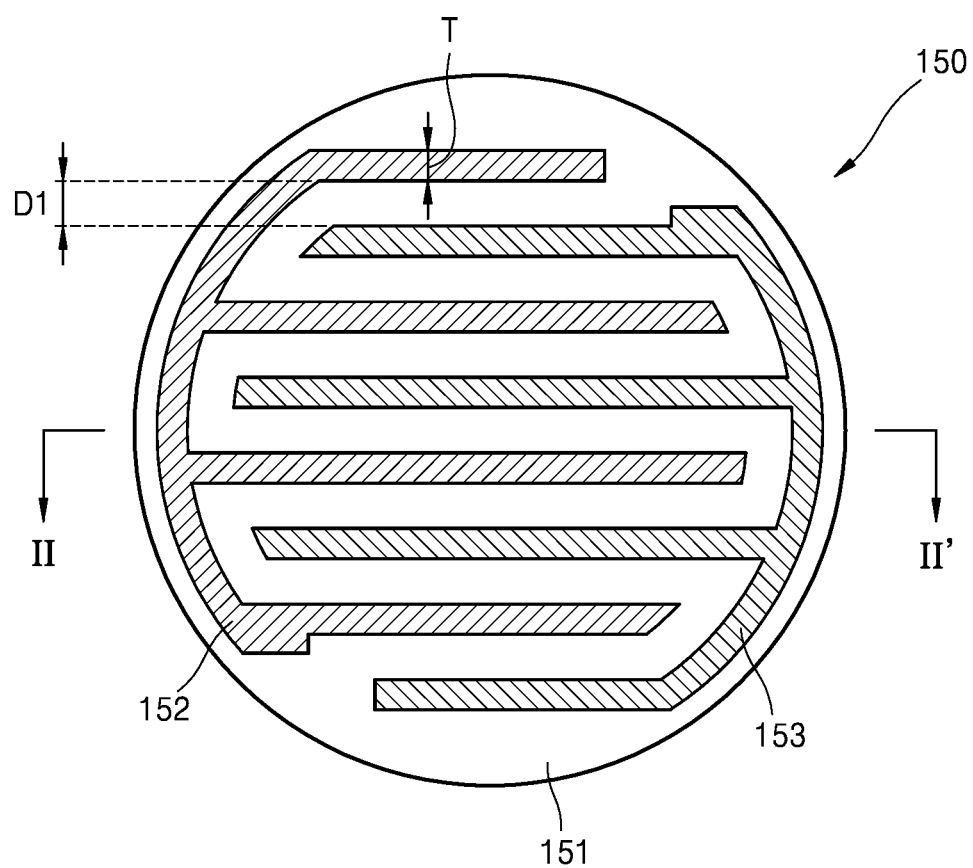
FIG. 4 is a plan view of a piezoelectric element of the contact lens of FIG. 1.
Figure 5:
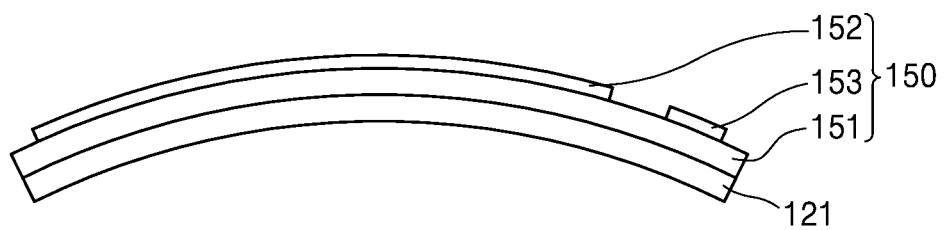
FIG. 5 is a sectional view of the piezoelectric element taken along line II-II' of FIG. 4.

FIG. 4 is a plan view of the piezoelectric element 150 of the contact lens of FIG. 1, and FIG. 5 is a sectional view of the piezoelectric element 150 taken along line II-II' of FIG. 4.

Referring to FIGS. 4 and 5, the piezoelectric element 150 includes a piezoelectric layer 151, and first and second electrodes 152 and 153 that contact the piezoelectric layer 151 and collect electricity generated due to deformation of the piezoelectric layer 151.

The piezoelectric layer 151 may be formed of a piezoelectric material, such as, BaTiO3, Lead Zirconate Titanate (PZT), or Polyvinylidene Fluoride (PVDF). The piezoelectric layer 151 may be formed to have a thickness of several μm to several tens of μm, and may be transparent with respect to visible light and be flexible. As will be described later, the piezoelectric layer 151 is deformed due to a pressure applied to the contact lens 100 worn between the eyelid and the eye according to an eyelid movement of the user, and accordingly produces electrical energy.

The first and second electrodes 152 and 153 are formed of a conductive material. For example, the first and second electrodes 152 and 153 may be formed of highly-conductive metal (such as gold or silver), transparent conducting oxide (TCO) (such as indium tin oxide (ITO)), or an amorphous metal oxide material (such as ZnO, InO, GaO, or SnO). The first and second electrodes 152 and 153 may be formed of a transparent electrode material, such as silver nanowires, carbon nanotubes (CNTs), graphene, or conducting polymer, or may be formed of a combination of the exemplified transparent electrode materials. As shown in FIG. 4, the first and second electrodes 152 and 153 may be arranged apart from each other on the piezoelectric layer 151. In addition, the first and second electrodes 152 and 153 may face each other, and may have comb electrodes arranged such that the first and second electrodes 152 and 153 elongate toward each other at a plurality of spots and alternate with each other. A separation distance between the first and second electrodes 152 and 153 is proportional to the voltage of electrical energy collected by the piezoelectric element 150, and thus may be determined in accordance with a required voltage size. For example, the separation distance D1 between the first and second electrodes 152 and 153 may be determined within the range of 100 μm to 500 μm. Because the first and second electrodes 152 and 153 are proportional to the current of electrical energy collected on an area (length) where they face each other, the first and second electrodes 152 and 153 in the comb structures secure a long area (length) where they face each other to thereby satisfy a required current size. In some cases, an alternating arrangement of the first and second electrodes 152 and 153 forms a lattice pattern and thus may perform a grating function (for example, polarized light filtering).

A width T of each of the first and second electrodes 152 and 153 may be appropriately designed according to the transparency of a material used to form the first and second electrodes 152 and 153. If the transparency of the material used to form the first and second electrodes 152 and 153 is low, the first and second electrodes 152 and 153 may have small widths in order to secure required transparency.

Figure 6:
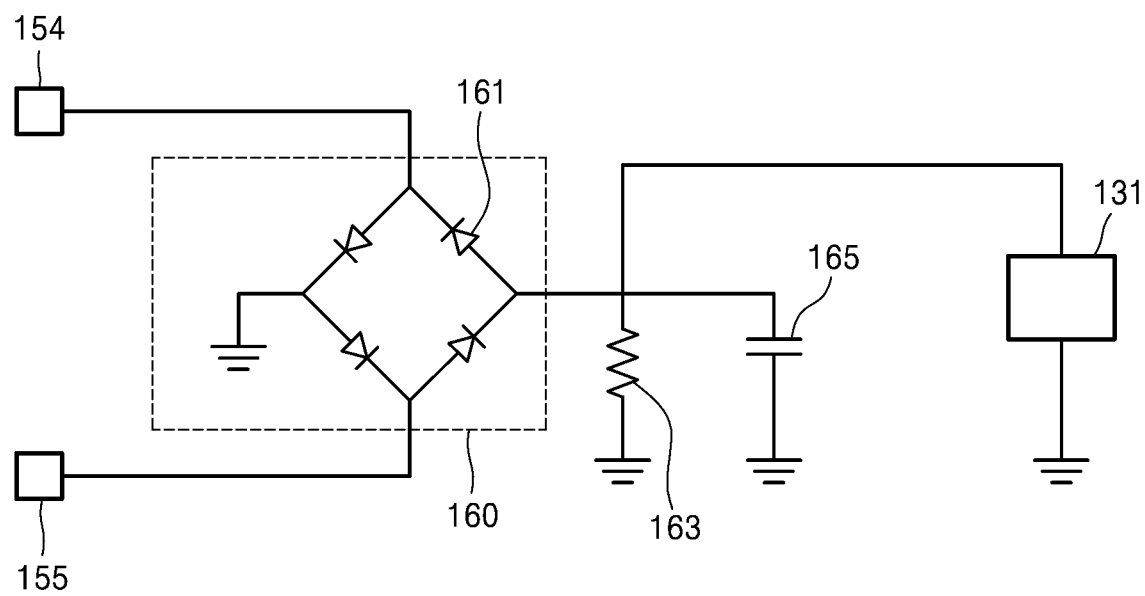
FIG. 6 is a circuit diagram of an example of a rectifying circuit in the contact lens of FIG. 1.
Figure 7:
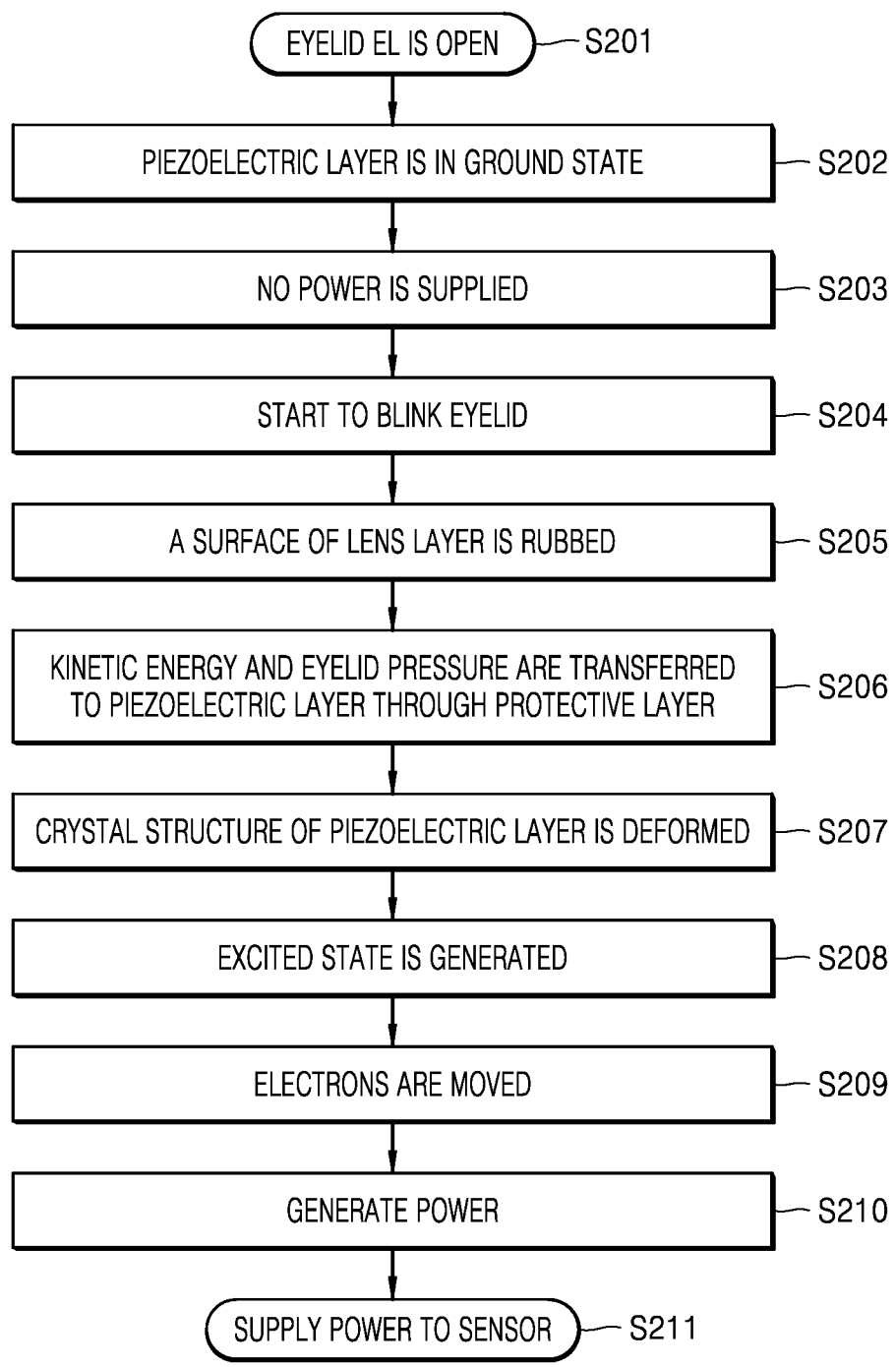
FIG. 7 is a flowchart of a current collecting operation of the contact lens of FIG. 1.
Figure 8A:
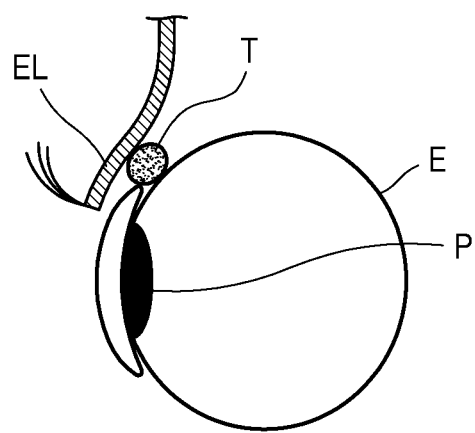
FIGS. 8A and 8B are views for explaining the current collecting operation of the contact lens of FIG. 1.
Figure 8B:
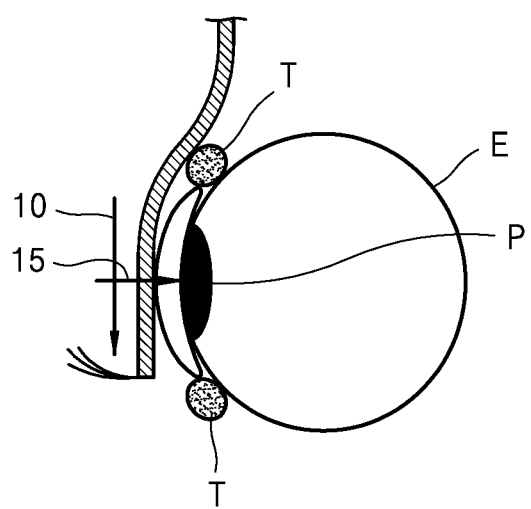
Figure 9:
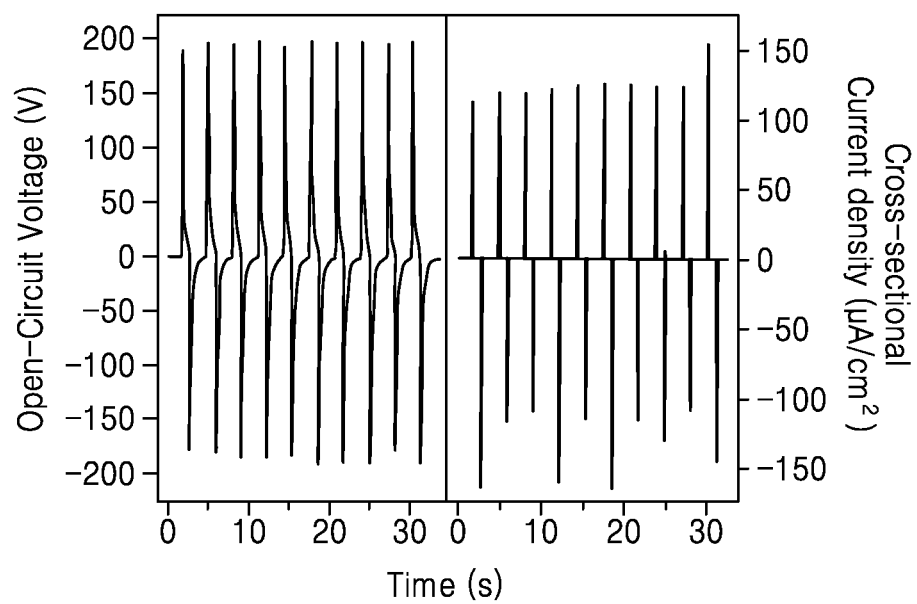
FIG. 9 is a graph showing a voltage signal generated by a piezoelectric element of FIG. 3.

FIG. 6 is a circuit diagram of the rectifying circuit 160 of the contact lens 100 according to the present embodiment. In FIG. 6, reference numerals 154 and 155 indicate electrode pads electrically connected to the first and second electrodes 152 and 153 of the piezoelectric element 150. As shown in FIG. 6, the rectifying circuit 160 may be implemented as a bridge circuit including diodes 161. The rectifying circuit 160 rectifies an alternating voltage of the electrical energy generated by the piezoelectric element 150, and stores the rectified alternating voltage in the power storage 165. The bridge circuit of FIG. 6 is an example of the rectifying circuit 160, and the present embodiment is not limited thereto. A well-known rectifying circuit may be employed. FIG. 7 is a flowchart of a current collecting operation of the contact lens 100, FIGS. 8A and 8B are views for explaining the current collecting operation of the contact lens 100 according to the present embodiment, and FIG. 9 is a graph showing a voltage signal generated by the piezoelectric element 150. In FIGS. 8A and 8B, reference character EL indicates an eyelid, reference character T indicates tear, reference character E indicates an eyeball, and reference character P indicates a pupil.

Referring to FIGS. 7-9, when the eyelid EL is open in operation S201, no external forces are applied to the piezoelectric layer 151 of the piezoelectric element 150, and accordingly the piezoelectric layer 151 is in a ground state, in operation S202. No power is supplied, in operation S203. When a user (i.e., a wearer of a contact lens) blinks the eyelid EL in operation S204, a surface 110a of the lens layer 110 is rubbed due to a movement of the eyelid EL and shrinkage of the muscle around the eyelid EL, in operation S205. Due to the rubbing of the eyelid EL, a predetermined pressure is applied to the surface 110a of the lens layer 110 and is transmitted to the piezoelectric element 150, in operation S206. When the piezoelectric element 150 is pressurized, a crystal structure of the piezoelectric layer 151 is deformed, in operation S207, an excited state is generated, in operation S208, and electrons are moved to the first and second electrodes 151 and 152 due to an electromotive force due to the generated excited state, in operation S209. The piezoelectric layer 151 of the piezoelectric element 150 generates an alternating voltage as the piezoelectric layer 151 repeats an operation of bending and spreading due to a movement of the eyelid, in operation S210. For example, the piezoelectric layer 151 is bent due to a closing movement of the eyelid, and accordingly, the piezoelectric element 150 may generate a positive (+) voltage, and the piezoelectric layer 151 is spread out due to an opening movement of the eyelid, and accordingly, the piezoelectric element 150 may generate a negative (−) voltage. As such, as the eyelid blinks, the positive voltage and the negative voltage may alternate with each other approximately once. In addition to such a movement of the eyelid, there may exist factors that make the piezoelectric element 150 be bent around the eye, such as a movement of an eyeball. The piezoelectric element 150 may also produce electrical energy due to these factors. The electrical energy generated by the piezoelectric element 150 may be rectified via the rectifying circuit 160, stored in the power storage 165, and the electrical energy may be supplied to the sensor 130, in operation S211.

Figure 10:
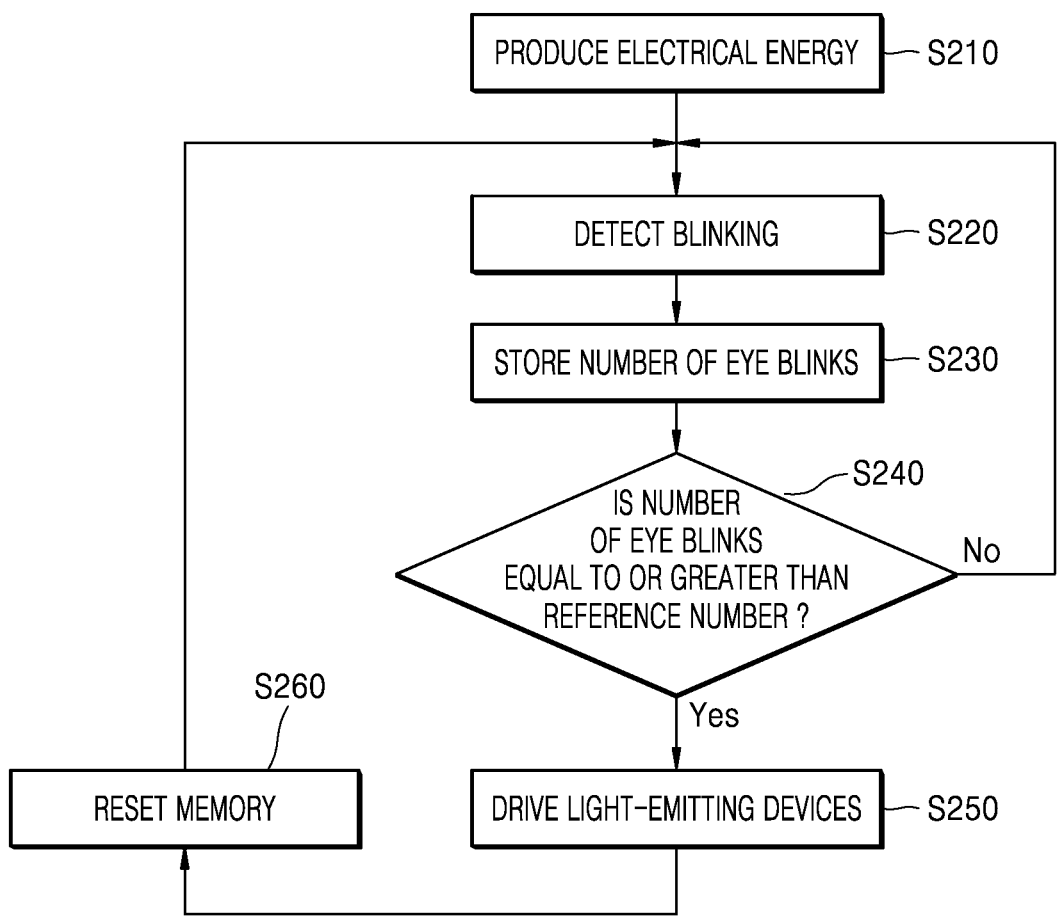
FIG. 10 is a flowchart of a method of driving the contact lens of FIG. 1.

FIG. 10 is a flowchart of a method of driving the contact lens of FIG. 1.

In operation S210, because the power 140 according to the present embodiment, namely, the piezoelectric element 150, the rectifying circuit 160, and the power storage 165, may be all implemented using passive devices, when a user wears the contact lens 100, the piezoelectric element 150 may immediately produce electrical energy without special manipulations or controls. When the electrical energy produced as described above reaches a sensing-enabling power amount, the sensor 130 detects blinking by using the produced electrical energy, in operation S220. When the electrical energy produced by the piezoelectric element 150 reaches a minimum power amount required to drive the sensor 130 (hereinafter, the sensing-enabling power amount), the sensor 130 may be automatically driven. For example, the sensor 130 may identify and count blinking by counting a peak in a waveform (see FIG. 9) of a voltage generated by the piezoelectric element 150. As another example, the sensor 130 may include a special photodiode (not shown) in order to detect blinking. If the eyelid is closed, light is blocked. If the eyelid is open, light reaches the photodiode. Thus, blinking may be detected by the photodiode. When the sensor 130 detects blinking, the memory 137 stores the number of eye blinks, in operation S230. Every time blinking is detected, the number of eye blinks stored in the memory 137 increases by 1. This eye blink counting may continuously repeat. When the number of eye blinks reaches a reference number, light-emitting devices of the display 135 are driven, in operation S250, and a value stored in the memory 137 is reset, in operation S260. Eye blink counting is repeated again.

For example, the number of eye blinks slightly varies according to persons, but the number of eye blinks of a normal person in daily lives is about 15 to about 20 per minute. Accordingly, approximate time may be counted based on the number of eye blinks. If the number of eye blinks detected by the sensor 130 reaches the reference number, the contact lens 100 drives the light-emitting devices of the display 135 to emit light, so that the user is informed that a certain period has passed. The contact lens 100 according to the present embodiment may be used when the user needs to be periodically informed of passage of time. If the user does a dangerous work or a periodically repeated work, the user may be informed that a predetermined time period has passed, and thus may be warned or may be informed that it is time to do a subsequent work.

Figure 11:
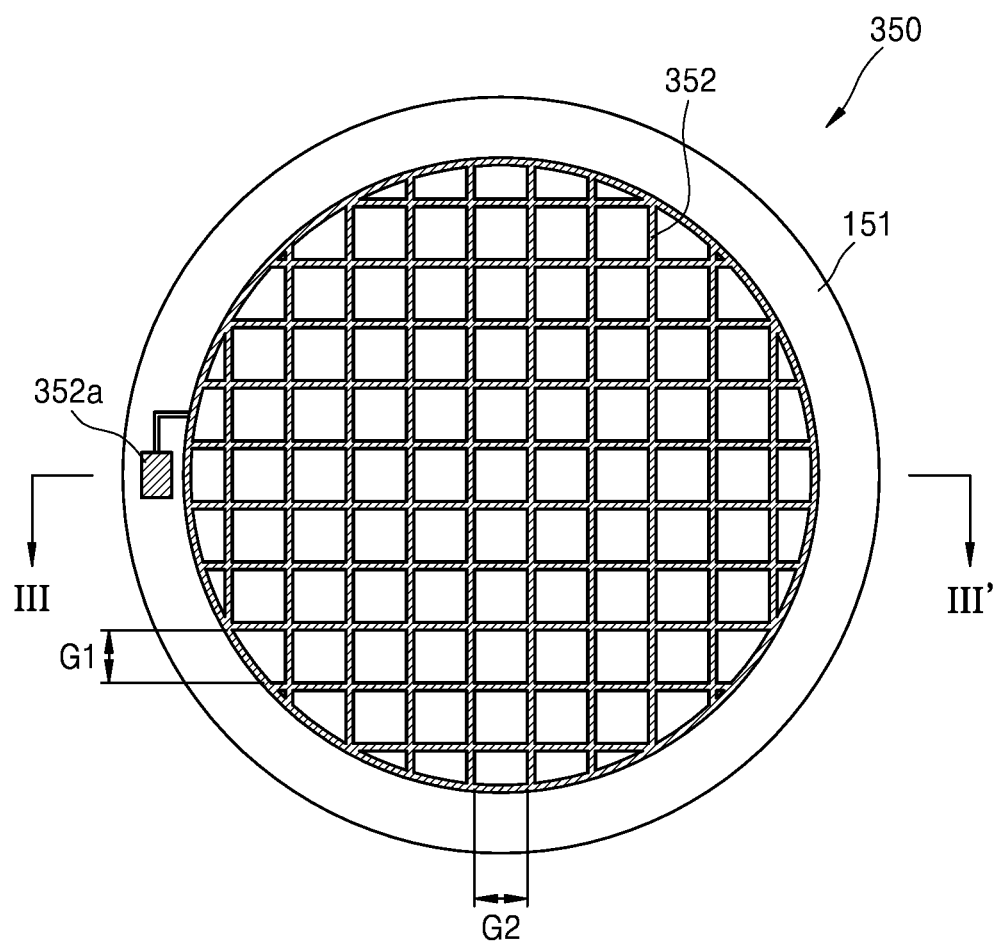
FIG. 11 is a plan view of a piezoelectric element of a contact lens according to another embodiment.

According to the above-described embodiment, the piezoelectric element 150 includes the first and second electrodes 151 and 152 formed on the same surface of the piezoelectric layer 151. However, the present invention is not limited thereto. FIG. 11 is a plan view of a piezoelectric element 350 of a contact lens according to another embodiment, and FIG. 12 is a sectional view of the piezoelectric element 350 taken along line III-III' of FIG. 11.

Figure 12:
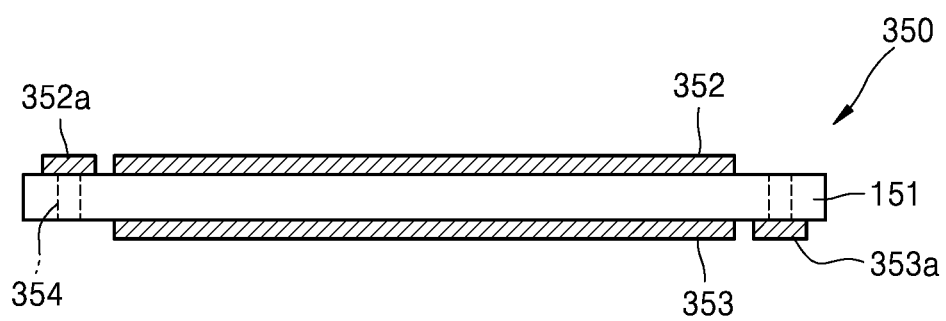
FIG. 12 is a sectional view of the piezoelectric element taken along line II-II' of FIG. 11.

Referring to FIGS. 11 and 12, the piezoelectric element 350 includes the piezoelectric layer 151, and first and second electrodes 352 and 353 respectively provided on both sides of the piezoelectric layer 151. As shown in FIG. 11, the first and second electrodes 352 and 353 may be formed as lattice patterns. Reference numerals 352a and 354 respectively indicate a pad for wiring of the first electrode 352 formed on an upper surface of the piezoelectric layer 151, and a via hole. When the first and second electrodes 352 and 353 have lattice patterns, a space between strips of a lattice may provide a pin hole effect. The pin hole effect refers to an effect in which a clear image is obtained by preventing generation of images at various locations by blocking some of the light beams that come via various paths. As such, the electrode patterns of the first and second electrodes 352 and 353 may be designed considering the pin hole effect. For example, grid distances G1 and G2 of the electrode patterns of the first and second electrodes 352 and 353 may be designed to be equal to or greater than 100 μm in order to secure a pin hole effect with respect to visible light.

Figure 13:
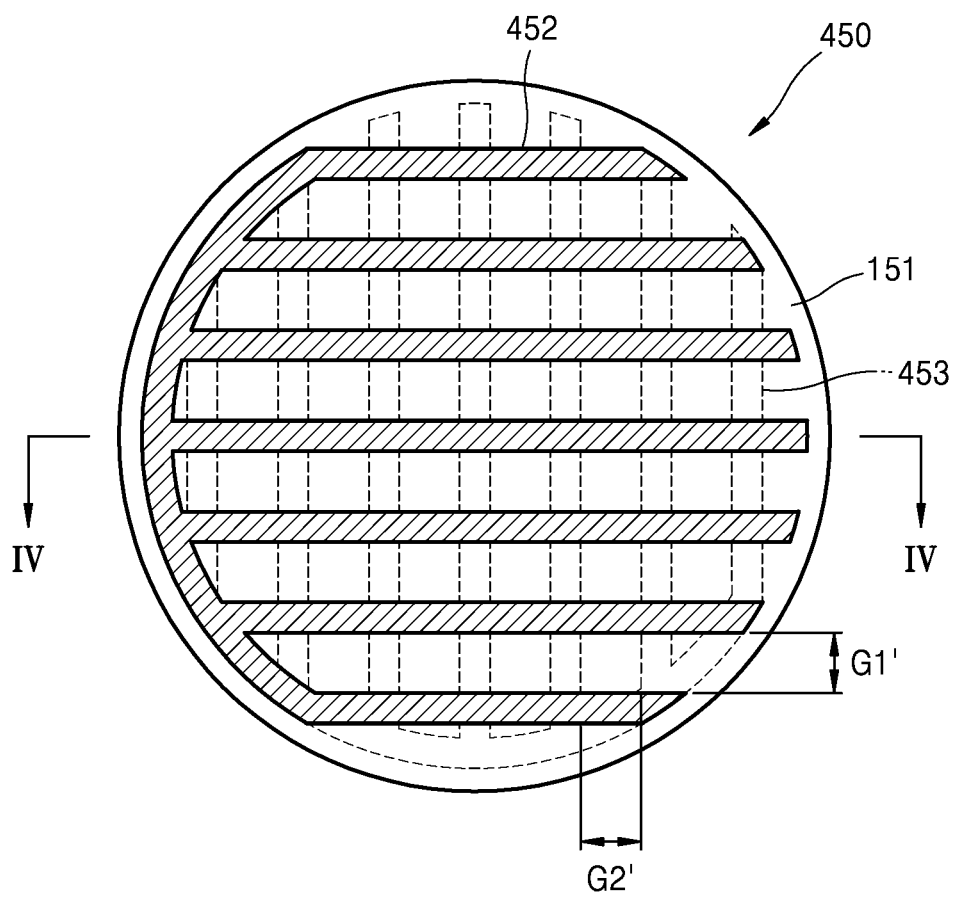
FIG. 13 is a plan view of a piezoelectric element of a contact lens according to another embodiment.
Figure 14:
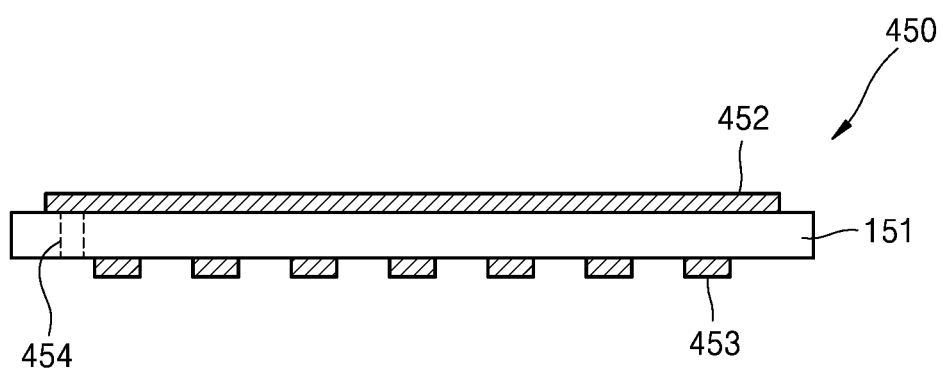
FIG. 14 is a sectional view of the piezoelectric element taken along line IV-IV of FIG. 13.

FIG. 13 is a plan view of a piezoelectric element of a contact lens according to another embodiment, and FIG. 14 is a sectional view of the piezoelectric element taken along line IV-IV' of FIG. 13.

Referring to FIGS. 13 and 14, the piezoelectric element 450 includes the piezoelectric layer 151, and first and second electrodes 452 and 453 respectively provided on both sides of the piezoelectric layer 151. The first electrode 452 may have a shape of a comb electrode that extends long in a first direction at a plurality of spots on one surface of the piezoelectric layer 151, and the second electrode 453 may have a shape of a comb electrode that extends long in a second direction at a plurality of spots on a back surface of the piezoelectric layer 151. The first direction and the second direction may intersect at 90°. Accordingly, as shown in FIG. 11, the first and second electrodes 452 and 453 cooperate with each other and form a lattice pattern as viewed from above. Thus, a grid distance G1' of the first electrode 452 and a grid distance G2' of the second electrode 453 may be designed in consideration of the pin hole effect. For example, the grid distance G1' of the electrode pattern of the first electrode 452 and the grid distance G2' of the electrode pattern of the second electrode 453 may be designed to be equal to or greater than 100 μm in order to secure a pin hole effect with respect to visible light.

Although the extending direction of the first electrode 452 and the extending direction of the second electrode 453 are perpendicular to each other in the present embodiment, the present invention is not limited thereto. For example, the extending direction of the first electrode 452 may be parallel to the extending direction of the second electrode 453, or the extending direction of the first electrode 452 may make an acute (obtuse) angle with the extending direction of the second electrode 453.

Although each of the first and second electrodes 452 and 453 extends long at a plurality of spots in the present embodiment, the present invention is not limited thereto. As another example, the first and second electrodes 452 and 454 may be formed in zigzag patterns.

Figure 15:
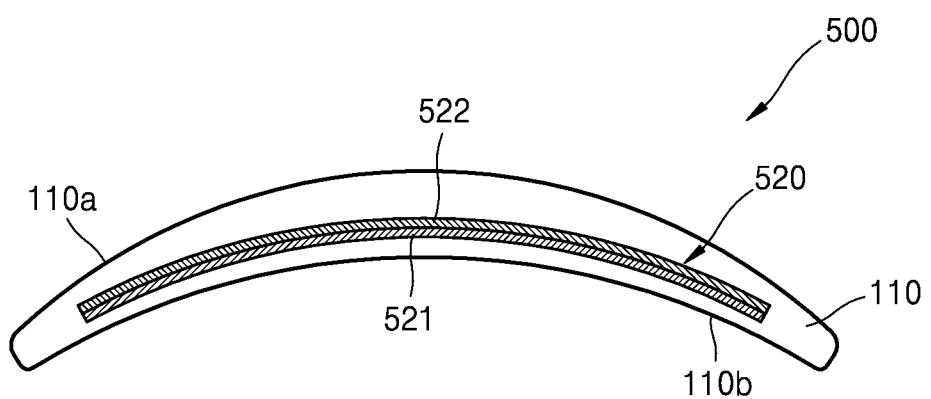
FIG. 15 is a sectional view of a contact lens according to another embodiment.

In the embodiment described above with reference to FIGS. 1-10, the sensor 130, and the rectifying circuit 160 and the power storage 165 of the power 140 are provided on the same layer on which the piezoelectric element 150 is formed. However, the present invention is not limited thereto. FIG. 15 is a sectional view of a contact lens 500 according to another embodiment. Referring to FIG. 15, a circuit thin film 520 constructing an electronic element unit may have a structure of a double layer formed of a circuit layer 521 and a piezoelectric element layer 522.

The piezoelectric element layer 522 may be positioned farther from a surface 110b of the lens portion 110 that directly contacts the eye of the user, than the circuit layer 521 is. In other words, when a user wears the contact lens 500, the piezoelectric element layer 522 is positioned to be exposed to the outside, and thus the piezoelectric element layer 522 may be more effectively deformed in accordance with a movement of the eyelid.

The circuit layer 520 may include all of the sensor 130 of FIG. 1, the rectifying circuit 160 of the power 140 of FIG. 1, and the power storage 165 of the power 140 of FIG. 1. Various circuit elements of the circuit layer 520 may be positioned outside of the circuit layer 520 in order to improve the transparency of the contact lens, but the present invention is not limited thereto. Transparency-secured circuit elements from among the various circuit elements of the circuit layer 520 may be positioned on a center of the circuit layer 520. The transparency refers to transparency in a visible band, and, even when there is an opaque portion, the opaque portion does not matter as long as the user does not feel uncomfortable when wearing the contact lens.

Figure 16:
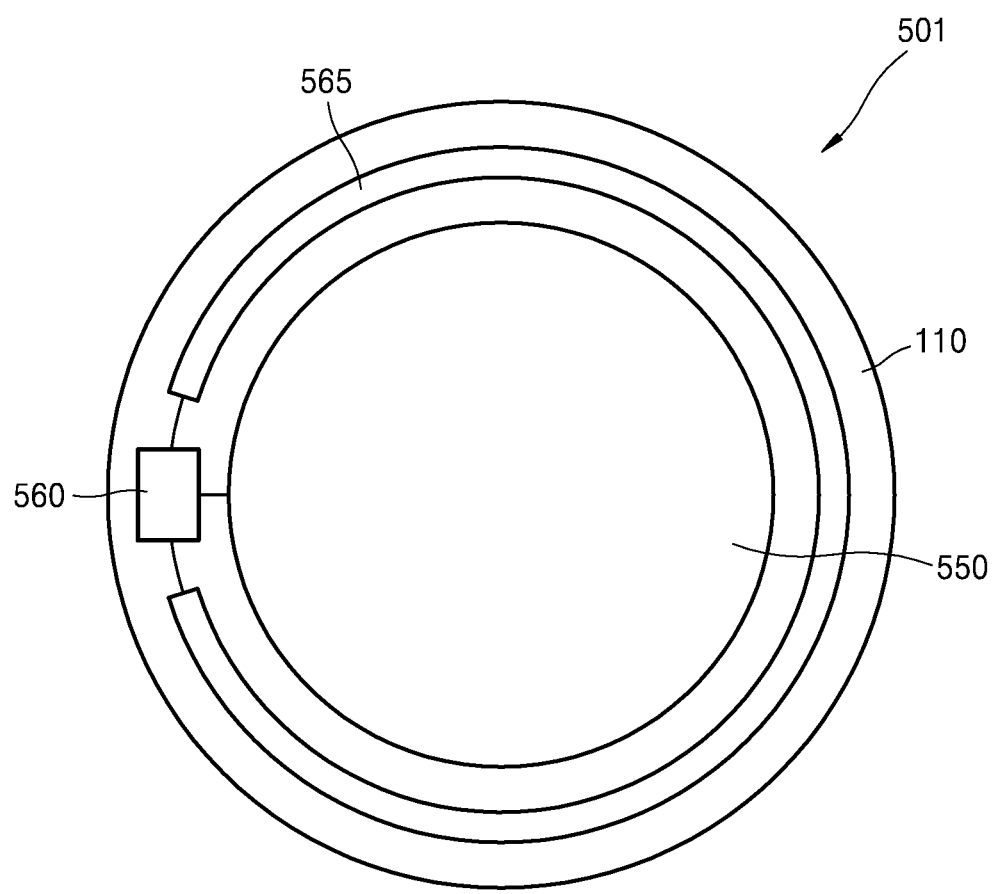
FIG. 16 is a plan view of a contact lens according to another embodiment.

Although the contact lens 500 of FIG. 15 has a structure of a double layer formed of the circuit layer 521 and the piezoelectric element layer 522, the present invention is not limited thereto. Some of the circuit elements included in the circuit layer 521 may be formed in the piezoelectric element layer 522. FIG. 16 is a plan view of a contact lens 501 according to another embodiment. Referring to FIG. 16, a rectifying circuit 560 and a power storage 565 may be formed on the same layer on which a piezoelectric element 550 is formed. The piezoelectric element 550 may be provided on a center region of the contact lens 501, and the rectifying circuit 560 and the power storage 565 may be provided on an outer region of the contact lens 501. Moreover, the power storage 565 may be a circular capacitor formed around the piezoelectric element 550. As shown in FIG. 15, a sensor (not shown) may be provided in the circuit layer 520 of FIG. 15.

Figure 17:
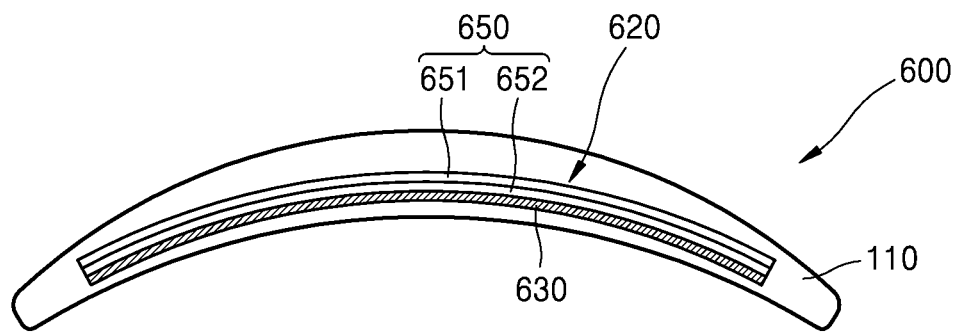
FIG. 17 is a side view of a contact lens according to another embodiment.

Although the piezoelectric element 150 includes the single piezoelectric layer 151 in the embodiments described above with reference to FIGS. 1-16, the present invention is not limited thereto. FIG. 17 is a side view of a contact lens 600 according to another embodiment, and FIG. 18 is a side view of a piezoelectric element layer 650 of FIG. 17.

Figure 18:
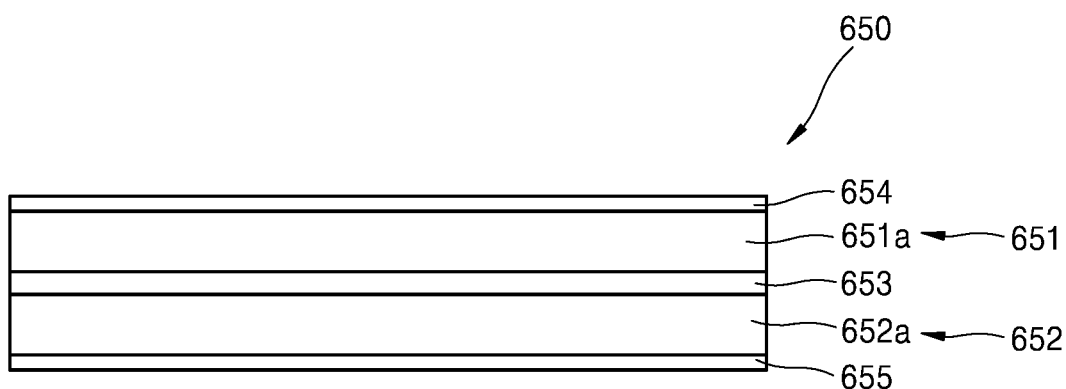
FIG. 18 is a side view of a piezoelectric element of FIG. 17.

Referring to FIGS. 17 and 18, a circuit thin film 620 that constitutes an electronic element unit in the contact lens 600 according to the present embodiment has a structure of a double layer formed of a circuit layer 630 and a piezoelectric element layer 650, and the piezoelectric element layer 650 includes a first piezoelectric element layer 651 and a second piezoelectric element layer 652. The piezoelectric element layer 650 may be positioned farther from a surface of the lens portion 110 that directly contacts the eye of the user, than the circuit layer 630 is. The first piezoelectric element layer 651 and the second piezoelectric element layer 652 may be stacked on the circuit layer 630. The first piezoelectric element layer 651 may include a first piezoelectric layer 651a, and first and second electrodes 653 and 654 respectively provided on both sides of the first piezoelectric layer 651a, and the second piezoelectric element layer 652 may include a second piezoelectric layer 652a, and the first electrode 653 and a third electrode 655 respectively provided on both surfaces of the second piezoelectric layer 652a. In this case, the first electrode 653 is between the first piezoelectric element layer 651 and the second piezoelectric element layer 652, and may be used as a common electrode for the first and second piezoelectric element layers 651 and 652. Of course, electrodes of each of the first and second piezoelectric element layers 651 and 652 may be formed on only one layer, similar to the electrode structure shown in FIG. 4. The above-described various types of electrode patterns may be used as an electrode pattern of each of the first and second piezoelectric element layers 651 and 652. The circuit layer 630 may include all of the sensor 130 of FIG. 1, the rectifying circuit 160 of the power 140 of FIG. 1, and the power storage 165 of the power 140 of FIG. 1. Various circuit elements of the circuit layer 630 may be positioned outside of the circuit layer 630 in order to improve the transparency of the contact lens, but the present invention is not limited thereto. Transparency-secured circuit elements from among the various circuit elements of the circuit layer 630 may be positioned on a center of the circuit layer 630.

Although the circuit layer 630 and the piezoelectric element layer 650 are formed on different layers in the present embodiment, the present invention is not limited thereto. Some of the circuit elements included in the circuit layer 630 may be provided on the same layer on which the piezoelectric element layer 650 is provided. In this case, the sensor layer 630 may be provided around the piezoelectric element layer 650.

Although the piezoelectric element layer 650 has a double-layer structure in the present embodiment, the present invention is not limited thereto. One of ordinary skill in the art may easily derive a multi-layer structure of three or more layers from the piezoelectric element layer 650 of the double-layer structure according to the present embodiment.

Figure 19:
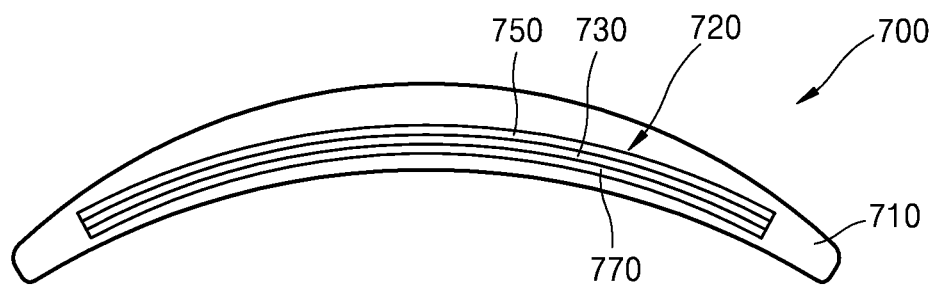
FIG. 19 is a schematic plan view of a contact lens according to another embodiment.

FIG. 19 is a schematic plan view of a contact lens 700 according to another embodiment.

A circuit thin film 720 that constitutes an electronic element unit in the contact lens 700 according to the present embodiment includes a circuit layer 730, a spacer 770, and a piezoelectric element layer 750. The spacer 770 may be provided between the circuit layer 730 of the circuit thin film 720 and the lens portion 710. Alternatively, the spacer 770 may be positioned between the piezoelectric element layer 750 and the circuit layer 730 of the circuit thin film 720. The spacer 770 may be an air layer, a liquid layer, or a soft material layer that is very flexible. The spacer 770 may include a plurality of columns (not shown) such that separation of upper and lower layers having the spacer 770 therebetween may be maintained. The spacer 770 reduces transmission of a stress generated according to a movement of the eyelid to a back side of the lens portion 710 or to the circuit layer 730 so that the piezoelectric element layer 750 located above the circuit layer 730 may be easily deformed according to a movement of the eyelid.

Figure 20:
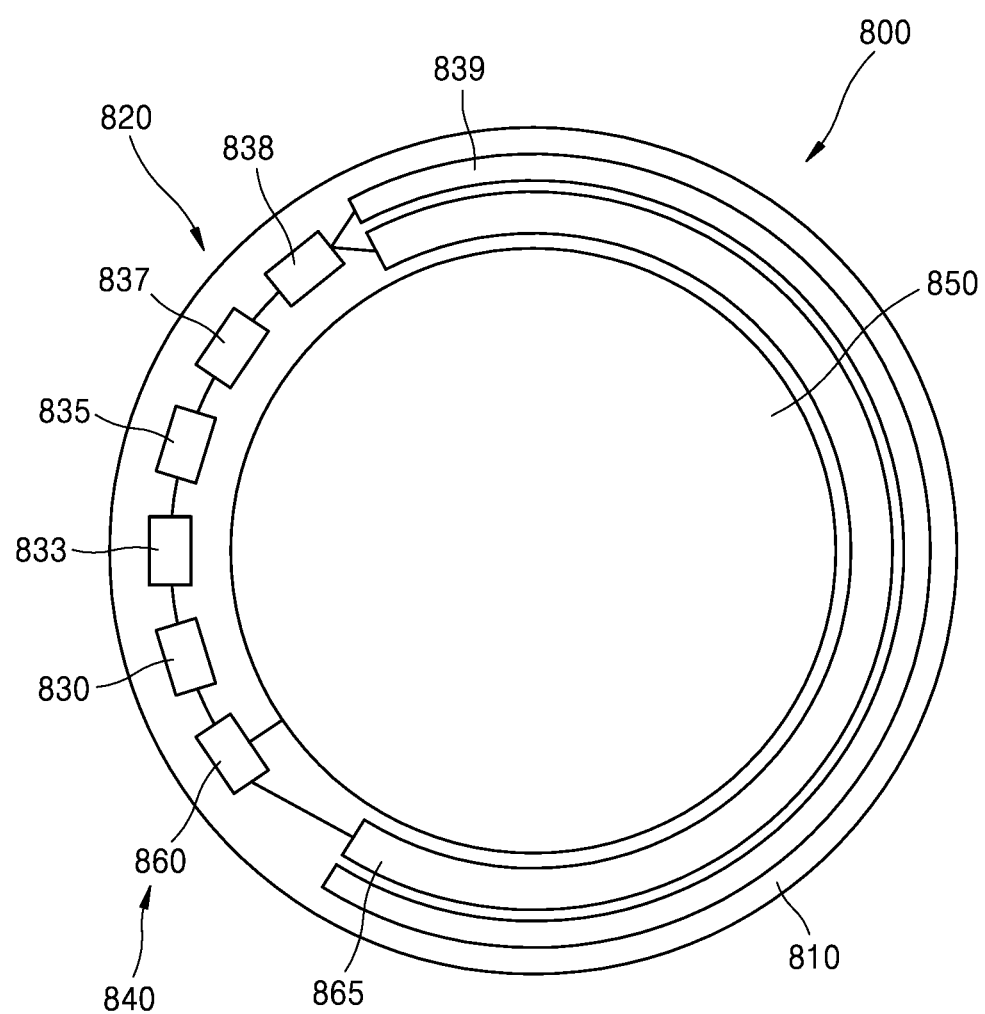
FIG. 20 is a schematic plan view of a contact lens according to another embodiment.
Figure 21:
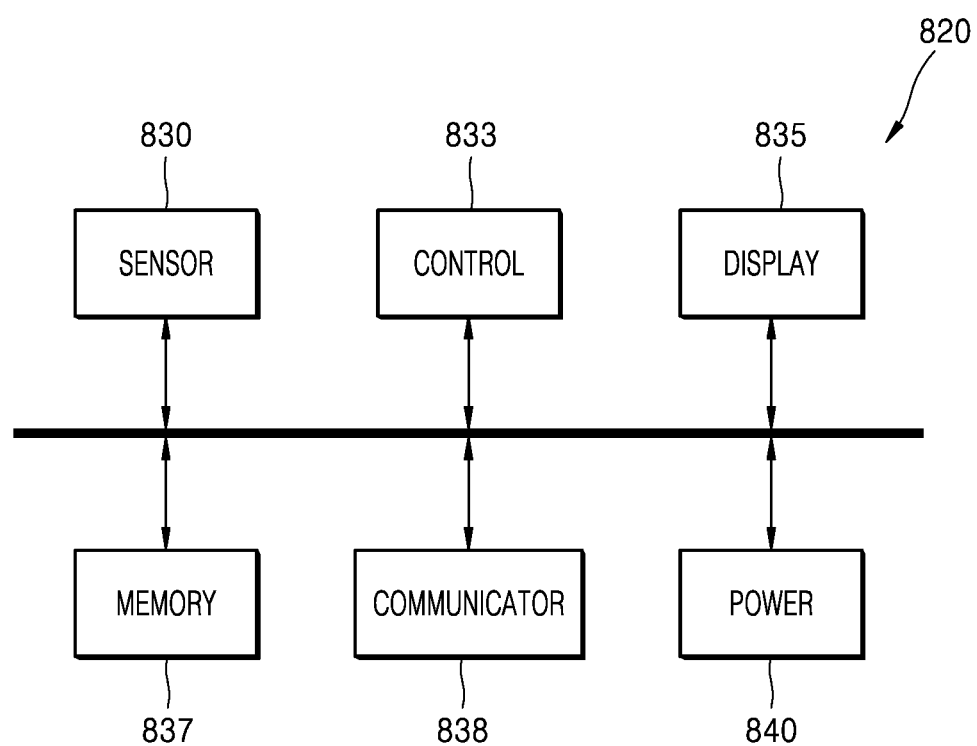
FIG. 21 is a schematic block diagram of a structure of an electronic element unit of the contact lens of FIG. 20.

FIG. 20 is a schematic plan view of a contact lens 800 according to another embodiment, and FIG. 21 is a block diagram of an electronic element unit 820 of the contact lens 800 of FIG. 20.

Referring to FIGS. 20 and 21, the contact lens 800 includes a lens portion 810, and the electronic element unit 820 provided in the lens portion 810. The electronic element unit 820 includes a sensor 830, a controller 833, a display 835, a memory 837, a communicator 838, and a power 840. The sensor 830, the control nit 833, the display 835, the memory 837, and the communicator 838 transmit and receive information or a control command via a data bus and may receive power from the power 840. Because components (for example, the lens portion 810) except for the components of the electronic element unit 820 may be substantially the same as the components of the above-described embodiments, detailed descriptions thereof will be omitted. Because components of the power 840 may be substantially the same as the components of the above-described embodiments, detailed descriptions thereof will be omitted.

The sensor 830 detects information of a user, and may include at least one of a bio sensor, a light-detection sensor, a gyro sensor, an inertia sensor, and a magnetic sensor.

For example, the bio sensor detects a bio material included in tears of the user, and may be, for example, a blood sugar detection sensor.

As another example, the sensor 830 may include at least one of an MEMS type gyro sensor and an MEMS type inertia sensor (or an acceleration sensor) and may detect a movement of the eyeball of the user. In other words, the sensor 830 may track the eye of the user by detecting a movement of the eyeball of the user. For example, a contact lens may include, as the sensor 830, a gyro sensor and a three-axis acceleration sensor and may track a movement of the pupil of the user or detect a moving location of the pupil by using signals detected from the gyro sensor and the three-axis acceleration sensor in combination. The acceleration sensor is a sensor that measures a specific force. Because a gravity acceleration is applied always downwards on the ground, when a positive (±) direction of a z axis indicates the center of the earth, the z axis of the acceleration sensor outputs a −g value while being perpendicular to the ground. When the inclination of a mounted object changes, the gravity affects not only a z-axis acceleration sensor but also x- and y-axis acceleration sensors. Just in case the contact lens moves in an arbitrary direction, a gyro sensor that measures a rotation angle may be used in combination with the acceleration sensor. The gyro sensor may be, for example, a 1 deg/hr-level (posture changes by one degree for one hour in a non-input state) MEMS type gyro sensor according to an algorithm that processes a signal. The MEMS type gyro sensor is generally a system that measures a rotation angle speed, and may read out a rotation angle speed during each sampling. In other words, a rotation angle may be a product of a rotation angle speed measured by a gyro sensor and a sampling time. A location of the contact lens may be tracked by updating a process of accumulating a rotation angle calculated by the gyro sensor from initially-detected roll, pitch, and yaw angles. A cumulative error of the gyro sensor may be compensated for by using the acceleration sensor together with the gyro sensor. For example, because the acceleration sensor can detect directly a roll and a pitch by using an output of the acceleration sensor, the acceleration sensor does not need to perform integration according to time. In addition, by using the acceleration sensor in combination with the gyro sensor, accumulation of an error according to an operating time except for a temperature and random walk noise may not occur. Because a yaw value detectable by the gyro sensor may also generate a cumulative error, the cumulative error with respect to the yaw value may be compensated for via a Kalman filter using a magnetic sensor.

As another example, the sensor 830 may count the number of eye blinks from the waveform of a voltage generated by the piezoelectric element 850, in consideration of the fact that an alternating waveform of the voltage generated by the piezoelectric element 850 corresponds to blinking of the eyelid. As another example, because external light is blocked as the eyelid blinks, the sensor 830 may include a light-detection sensor, such as a photodiode, and may count the number of eye blinks from a signal input to the light-detection sensor. The number of eye blinks per time has variations according to persons, but a wearer in a calm state may have a constant number of eye blinks per time. Accordingly, when the circuit thin film 820 does not include a special timer, the number of eye blinks may be used as an approximate time reference. In addition, the number of eye blinks may vary according to a fatigue status, a tension status, and the like of the wearer. Accordingly, as will be described later, a current status of the wearer may be ascertained by periodically transmitting information about the number of eye blinks to an external device that interoperates with the contact lens. Moreover, the sensor 830 may detect a duration of eye-closing of the user or a time interval between eye-closing and eye-closing.

The controller 833 controls all operations of the contact lens. For example, the controller 833 may control the sensor 830, the display 835, and the communicator 838 by executing programs stored in the memory 837.

For example, the controller 833 may count blinking from the waveform of the voltage generated by the piezoelectric element 850 and may control the number of eye blinks to be stored in the memory 837.

As another example, the controller 833 may drive the sensor 830 every a predetermined number of eye blinks. As another example, the controller 833 may determine whether the amount of power stored in the power storage 865 satisfies a minimum power amount required to drive the sensor 830 (hereinafter, a sensing-enabling power amount). If the stored power amount is equal to or greater than the sensing-enabling power amount, the controller 833 may control the sensor 830 to operate on a regular basis.

As another example, the controller 833 may determine whether the amount of power stored in the power storage 865 satisfies a minimum power amount necessary for communication (hereinafter, a communication-enabling power amount). If the stored power amount is equal to or greater than the communication-enabling power amount, the controller 833 may control the communicator 838 to communication with an external device.

As another example, when the controller 833 receives a data transmission command from the external device, the controller 833 may transmit data stored in the memory 837, and, when the controller 833 receives a reception-completion response from the external device, the controller 833 may remove data from the memory 837 in order to perform a reset operation.

As another example, the controller 833 may perform a series of control operations corresponding to a blinking pattern of the user. For example, given that a case where a duration of eye-closing is long is referred to as a first eye blink and a case where a duration of eye-closing is short is referred to as a second eye blink, the controller 833 may generate a character in accordance with various combinations of first eye blinks and second eye blinks and transmit the character to the outside, or perform a control (for example, an attempt of communication with the outside, or measurement of a blood sugar concentration via the sensor 830).

The memory 837 stores a series of control commands of operating the controller 833, or store information measured by the sensor 830. When the information measured by the sensor 830 exceeds a storage capacity of the memory 837, the memory 837 may sequentially delete oldest information and store recent measured information. The memory 837 may be, for example, non-volatile memory.

The display 835 may display information of the user detected by the sensor 830. The display 835 may include a light-emitting device and a driving circuit of the light-emitting device. Depending on the type of a light-emitting device, a driving circuit may be omitted. The light-emitting device may be, for example, an LED or an OLED. For example, a contact lens may check a dangerous situation faced by the body of a current wearer by comparing raw data or processed information of the information obtained by the sensor 830 embedded in the contact lens with a reference value at regular intervals while periodically storing the raw data or the processed information. In this case, the contact lens according to the present embodiment may warn the user by using the display 835 embedded therein.

Figure 22:
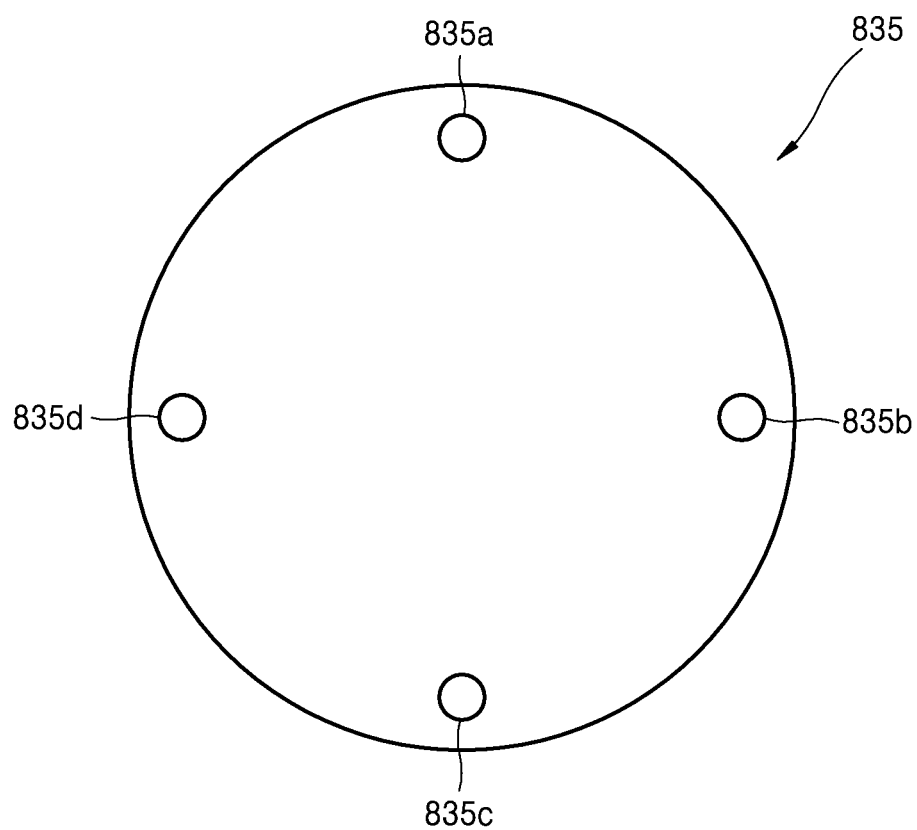
FIG. 22 illustrates an example of a display of the contact lens of FIG. 20.

FIG. 22 is a schematic diagram of an example of the display 835. Referring to FIG. 22, the display 835 may include four light-emitting devices 835a, 835b, 835c, and 835d. Some materials of the light-emitting devices 835a, 835b, 835c, and 835d may be opaque. In this case, when a contact lens is worn, the light-emitting devices 835a, 835b, 835c, and 835d may be arranged around the pupil, namely, along the outer circumference of the contact lens. The four light-emitting devices 835a, 835b, 835c, and 835d may be arranged at intervals of 90 degrees. The four light-emitting devices 835a, 835b, 835c, and 835d may independently emit light. The four light-emitting devices 835a, 135b, 135c, and 135d may be, for example, LEDs or OLEDs. Although light emitted from the light-emitting devices 835a, 835b, 835c, and 835d is diffused while being reflected within the lens portion 810, neighborhoods of the light-emitting devices 835a, 835b, 835c, and 835d are brighter. Accordingly, information may be transmitted to the user by using a light-emitting pattern of the light-emitting devices 835a, 835b, 835c, and 835d. The arrangement of the four light-emitting devices 835a, 835b, 835c, and 835d is an example, and the present embodiment is not limited thereto. For example, the display 835 may include a single light-emitting device or a ring-shaped light-emitting device.

Figure 26:
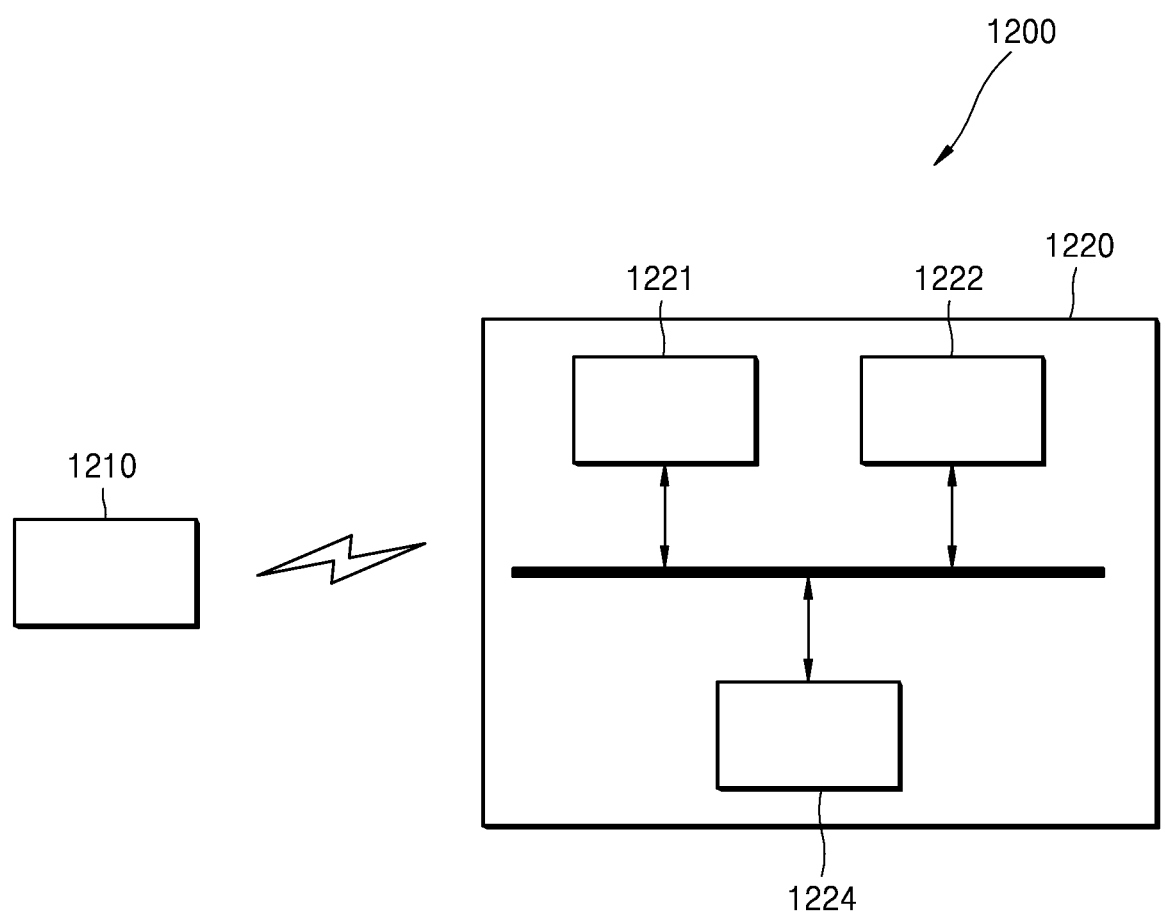
FIG. 26 is a block diagram of a system including a contact lens according to an embodiment.

Referring back to FIG. 20, the communicator 838 wirelessly communicates with an external device 1220 of FIG. 26 via an antenna 839, and thus may transmit information detected by the sensor 830 to the external device 1220. Moreover, the communicator 838 may receive a control command from the external device 1220. The antenna 839 may be formed in a ring shape that surrounds the piezoelectric element 850. As in the above-described embodiment, the power storage 865 may be implemented using a ring-shaped capacitor. In this case, the antenna 839 may be arranged around the power storage 865 and may minimize a radio wave directivity influence due to the power storage 865. Of course, the antenna 839 is not limited to this ring shape. The antenna 839 may be formed in a predetermined pattern, or a portion of a ring shaped antenna 839 may have a pattern. Moreover, a portion of the power storage 865 may be utilized as the antenna 839.

Although the electronic element unit 820 has a single-layer structure in the present embodiment, the present invention is not limited thereto. For example, the antenna 839 and the power storage 865 may be provided on different layers. For example, the antenna 839 may be disposed around the piezoelectric element 850 on the same layer on which the piezoelectric element 850 is disposed, and the power storage 865 may be disposed on a different layer than the layer on which the piezoelectric element 850 is disposed. Alternatively, the power storage 865 may be disposed around the piezoelectric element 850 on the same layer on which the piezoelectric element 850 is disposed, and the antenna 839 may be disposed on a different layer than the layer on which the piezoelectric element 850 is disposed.

Figure 23:
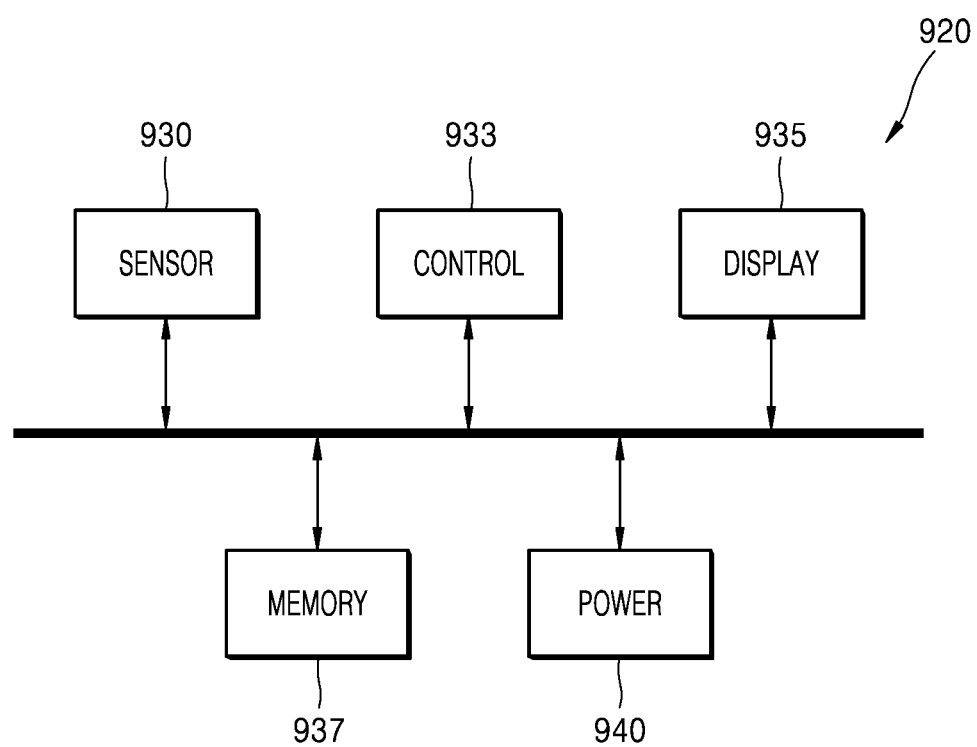
FIG. 23 is a schematic plan view of a contact lens according to another embodiment.

Although a communicator is included in the present embodiment, the present invention is not limited thereto. FIG. 23 is a block diagram of an electronic element unit 920 of a contact lens according to another embodiment. Referring to FIG. 23, the electronic element unit 920 of the contact lens according to the present embodiment includes a sensor 930, a controller 933, a display 935, a memory 937, and a power 940. The electronic element unit 920 according to the present embodiment may be understood as omitting the communicator 838 and the antenna 839 from the electronic element unit 820 described above with reference to FIGS. 20-22. Information detected by the sensor 930 may be displayed on the display 935. For example, the controller 933 may assist a wearer in counting a rough time period, by storing the number of eye blinks in the memory 937 and performing a display (for example, activating the light-emitting devices 835a, 835b, 835c, and 835d of FIG. 22 to emit light) on the display 935 every a predetermined number of eye blinks. In the case that the sensor 930 is a bio sensor, such as a blood sugar detection sensor, the controller 933 may calculate a blood sugar of a user by analyzing a signal detected by the sensor 930, and control the display 935 to indicate that the blood sugar and the like makes the user in danger, when an estimated blood sugar exceeds a predetermined threshold.

Figure 24A:
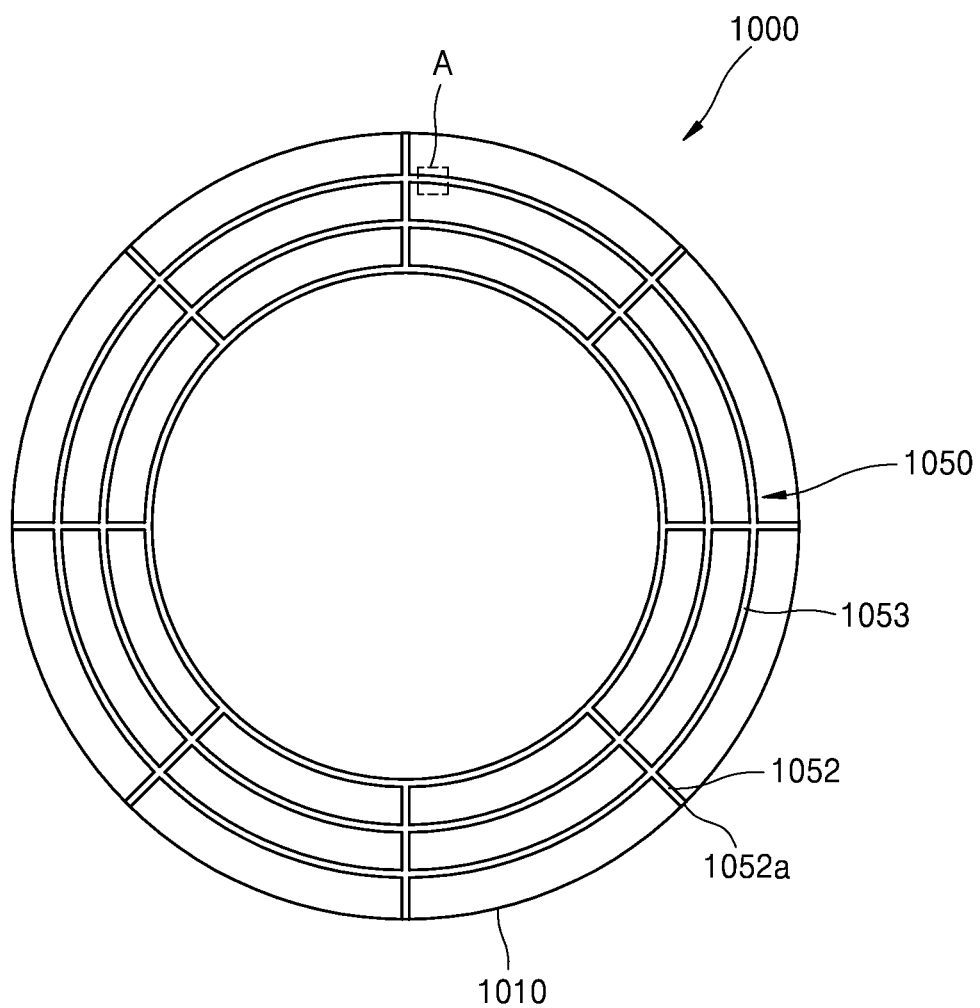
FIG. 24A is a schematic plan view of a contact lens according to another embodiment.
Figure 24B:
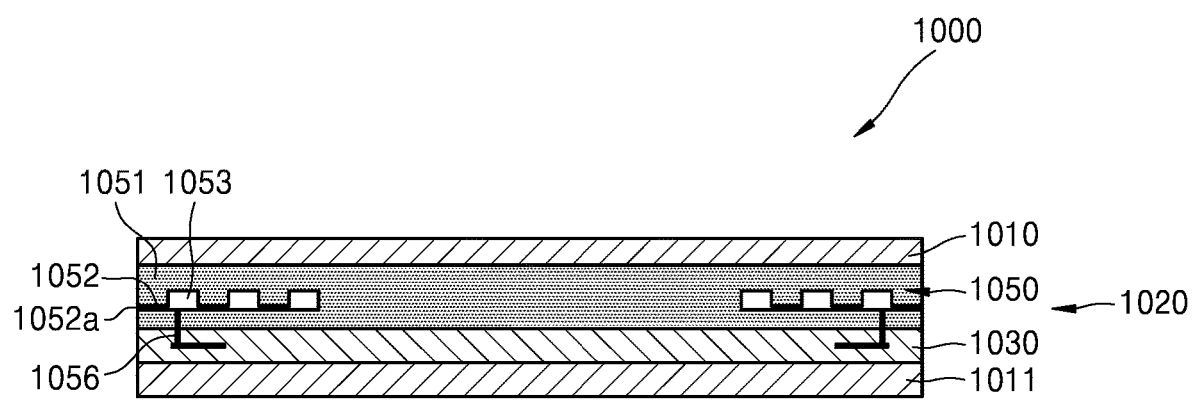
FIG. 24B is a sectional view of the contact lens of FIG. 24A FIGS. 25A and 25B are magnified views of examples of a biofuel cell of the contact lens of FIG. 20.

FIG. 24A is a schematic plan view of a contact lens 1000 according to another embodiment, and FIG. 24B is a sectional view of the contact lens 1000 of FIG. 24A.

Referring to FIGS. 24A and 24B, the contact lens 1000 includes lens portions 1010 and 1011, a circuit 1030 positioned within the lens portions 1010 and 1011, and a power. Although the lens portions 1010 and 1011 are illustrated as two layers in FIG. 24B, the lens portions 1010 and 1011 may be a single lens body.

The circuit 1030 may include a sensor (see the sensor 130 of FIG. 1, the sensor 830 of FIG. 21, or the sensor 930 of FIG. 23) that detects biometric information of a user. The circuit 1030 may further include a display (see the display 135 of FIG. 1, the display 835 of FIG. 21, or the display 935 of FIG. 23) that displays the biometric information detected by the sensor or other pieces of information. The circuit 1030 may further include a controller (controller 833 of FIG. 21), a memory (memory 837 of FIG. 21), and a communicator (communicator 838 of FIG. 21) and thus may process the biometric information detected by the sensor or communicate with an external device. Some of the display, the controller, the memory, and the communicator may be omitted. The structure of the circuit 1030 is substantially the same as corresponding structures in the above-described embodiments, and thus detailed description thereof will be omitted.

The power may include a biofuel cell 1050. The power may further include a power storage (see the power storage 165 of FIG. 1) that stores electrical energy generated by the biofuel cell 1050). The power storage may include a capacitor, such as an ultra-small super capacitor, and may be provided along outer circumferences of the lens portions 1010 and 1011. In FIG. 24B, reference numeral 1056 indicates a wiring line that transmits the electrical energy obtained by the biofuel cell 1050 to the circuit 1030.

The biofuel cell 1050 is another example of an energy harvesting unit that produces electrical energy from biochemical energy generated via a reaction of a small amount of a component included in tear with an electrode, namely, that performs harvest. The biochemical energy may include at least one of bioenergy and chemical energy. For example, the biofuel cell 10:50 may produce the electrical energy by using enzymes or microbes in a small amount of sugar or minerals included in tear.

The biofuel cell 1050 may include a collector that collects tear. The collector includes one or a plurality of microtubes 1053 having a ring shape and provided within the lens portion 1010, and a micro tear-tube 1052 extending in a diameter direction from an outer edge of the lens portion 1010 toward the microtubes 1053.

The micro tear-tube 1052 may be fine enough to induce a capillary phenomenon and may be larger than a molecular size of a material of tear that is to be utilized. An end 1052*a* of the micro tear-tube 1052 is exposed to the outside of the lens portion 1010 such that tear can be introduced into the micro tear-tube 1052.

Figure 25A:
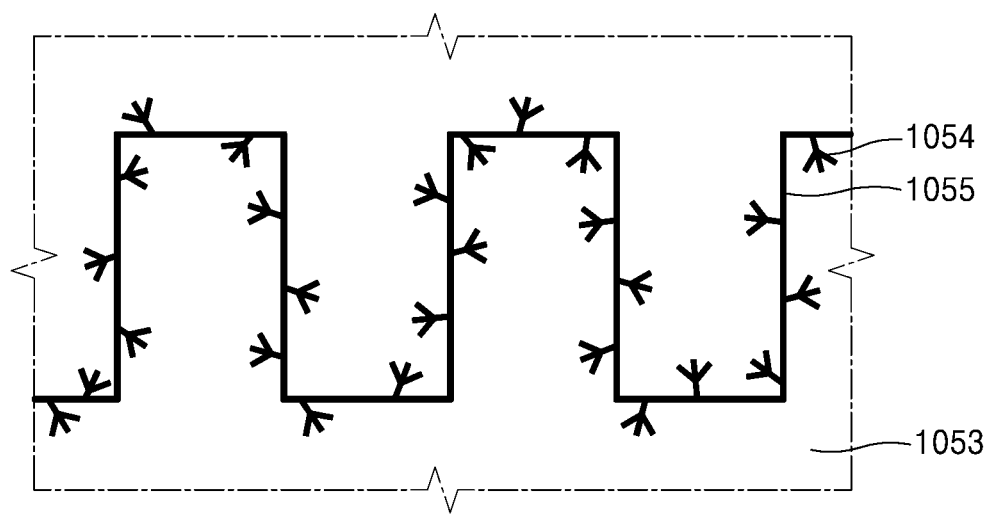
Figure 25B:
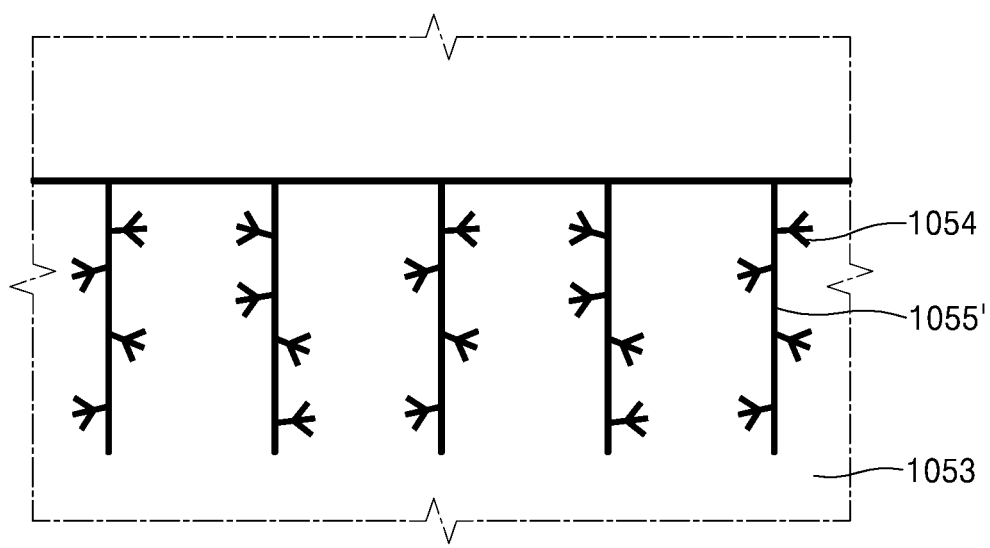

The microtubes 1053 receive tear from the micro tear-tube 1052. In the microtubes 1053, biochemical energy is transformed into electrical energy via an oxidation-reduction reaction. The microtubes 1053 may have a wrinkle space that is wider twice or more than a molecular size of a material intended to react with microbes or enzymes, in order to maximize the reaction with the microbes or enzymes. FIGS. 25A and 25B are magnified views of a portion A of the contact lens 1000 of FIG. 24A and illustrate examples of a wrinkle space of a microtube 1053 of the biofuel cell 1050. The microtube 1053 may include a zigzagged electrode 1055 as shown in FIG. 25A or may include an electrode 1055' having a plurality of side branches as shown in FIG. 25B. Receptors 1054 that are to be utilized in a reaction are arranged in the electrodes 1055 and 1055' of the microtube 1053. The receptors 1054 may use enzymes or microbes as a catalyst. The electrodes 1055 and 1055' may be understood as negative electrodes (or positive electrodes) to which the receptors 1054 are fixed and thus in which an oxidation or reduction reaction occurs. Counter electrodes may be provided on inner walls of the microtubes 1053 so as to be opposite to the electrodes 1055 and 1055'.

In the microtubes 1053, an organic material included in tear may biologically react with the receptors 1054, and thus electrical energy may be produced via an oxidation reaction in a positive electrode or a reduction reaction with oxygen in a negative electrode. For example, when glucose oxidase (GOx) as the receptors 1054, namely, a catalyst, is attached to the electrodes 1055 and 1055', the GOx accelerates oxidation of glucose included in tear to thereby obtain electrons. For example, an output of 1.02 mW per unit area to a 50 μm fiber electrode under a human blood serum condition is being reported.

The electrons collected in the electrodes 1055 and 1055' via the receptors 1054 may be transmitted to the circuit 1030 via the wiring line 1056 and stored in the power storage, or may be transmitted directly to the sensor and thus drive the sensor. In the above-described embodiment, the micro tear-tube 1052 and the microtubes 1053 are an example of a collector that collects tear. However, the present invention is not limited thereto. As another example, an outermost surface of the lens portion 1010 may have a porous structure, and receptors may be provided within the porous outermost surface. In this case, when tear is introduced into the porous outermost surface, electrical energy may be produced via an oxidation-reduction reaction. As another example, the outermost surface of the lens portion 1010 may be formed of an oxidative combination from which a molecular binding structure is separable in a specific situation. In this case, the electrode of a biofuel cell in which an oxidation-reduction reaction occurs may be understood as having been formed on the outermost surface of the lens portion 1010 without including a special collector that collects tear.

The biofuel cell according to the above-described embodiment has been described above as an example of producing electrical energy from the organic material included in tear, but the present invention is not limited thereto. As another example, the electrical energy may be produced via a chemical reaction with an inorganic material included in tear, such as salt.

The biofuel cell according to the above-described embodiment has a similar structure to a room temperature type fuel cell in terms of principle, and enzyme or microbes (*Shewanella* bacteria or the like) capable of reacting with sugar and a lipid component included in tear may be used as a catalyst. A material produced via a biological reaction of an organic material, such as glucose, is oxidized in a positive electrode, and electrical energy is produced via a reduction reaction of the organic material with oxygen in a negative electrode.

The contact lenses according to the above-described embodiments have been described above as obtaining electrical energy via an energy harvesting unit included therein. However, the contact lenses may receive the electrical energy from the outside, together with the energy harvesting unit. For example, a contact lens may further include a wireless power reception module, and thus may receive electrical energy in the form of an electrical field, a magnetic field, or an electromagnetic field from the outside.

FIG. 26 is a block diagram of a system 200 including a contact lens according to an embodiment.

Referring to FIG. 26, the system 1200 according to the present embodiment includes a contact lens 1210, and an external device 1220 that communicates with the contact lens 1210.

The external electronic device 1220 includes a communicator 1221, a controller 1222, and a memory 1224.

A communicator (communicator 838 of FIG. 21) of the contact lens 1210 and the communicator 1221 of the external electronic device 1220 may include a short-distance communication module. The short-distance communication module denotes a module for short-distance communication within a predetermined distance. For example, short-distance communication technology may be a wireless local area network (WLAN), Wi-Fi, Bluetooth, ZigBee, Wi-Fi Direct (WFD), ultra wideband (UWB), infrared Data Association (IrDA), Bluetooth Low Energy (BLE), Near Field Communication (NFC), or the like, but the present invention is not limited thereto. The communicator 838 of the contact lens 1210 and the communicator 1221 of the external electronic device 1220 may employ a mobile communication module or any other well-known wireless communication method.

The electronic device 1220 may always connect to the contact lens 1210 and thus process information received from the contact lens 1210 in real time. Alternatively, the electronic device 1220 may connect to the contact lens 1210 at regular time intervals, or may connect thereto at a specific time and receive information from the contact lens 1210 periodically or sporadically and process the received information. The electronic device 1220 may be a mobile telephone, a smartphone, a charging pad, a tablet computer, a personal digital assistant (PDA), an electronic-book terminal, a digital broadcasting terminal, a laptop computer, a personal computer (PC), a navigation, an MP3 player, a digital camera, an Internet Protocol Television (IPTV), a Digital Television (DTV), a game player, a remote controller, a CE apparatus (for example, a refrigerator or an air conditioner having a communication function), or an automobile, but the present invention is not limited thereto. The electronic device 1220 may be a wearable device that can be worn by a user. For example, the electronic device 1220 according to an embodiment of the present invention may be implemented using a watch, glasses, a ring, a bracelet, a necklace, or the like.

For example, the information received from the contact lens 1210 may be information about a movement of the eye of the user. In this case, the controller 1222 may extract at least one of a direction of the movement of the eye of the user and a degree of the movement, based on the information about the movement of the eye of the user, and generate a first control command corresponding to the at least one of the direction of the movement of the eye of the user and the degree of the movement. The first control command may be a control command for the electronic device 1220 or a control command for another electronic device. For example, the controller 1222 may classify movements of the eye of the user into a left movement, a right movement, an up movement, and a down movement, and generate control commands respectively corresponding to the left, right, up, and down movements.

As another example, the information received from the contact lens 1210 may be information about blinking of the user. The controller 1222 may extract at least one of the number of eye blinks per unit time and a duration of an eye blink, based on the information about the blinking of the user, and generate a second control command corresponding to the at least one of the number of eye blinks per unit time and the duration of an eye blink. The second control command may be a control command for the electronic device 1220 or a control command for another electronic device. For example, when the number of eye blinks during a predetermined time period exceeds a predetermined reference number or the duration of an eye blink exceeds a predetermined reference time period, the controller 1222 may generate a specific control command.

As another example, the information received from the contact lens 1210 may be the information about the blinking of the user, and the controller 1222 may detect a fatigue degree of the user, based on the information about the blinking of the user, and may generate a third control command when the fatigue degree of the user exceeds a reference value. The third control command may be a control command of generating an alarm that warns the user.

As another example, the information received from the contact lens 1210 may be information (e.g., blood sugar) about a biomaterial included in tear, and the controller 1222 may generate information about a bio status of the user, based on the information about the biomaterial. The information about the bio status may be accumulated and used as health management data of the user.

FIGS. 27A-27F are views for explaining a method of manufacturing a contact lens, according to an embodiment.

Figure 27A:
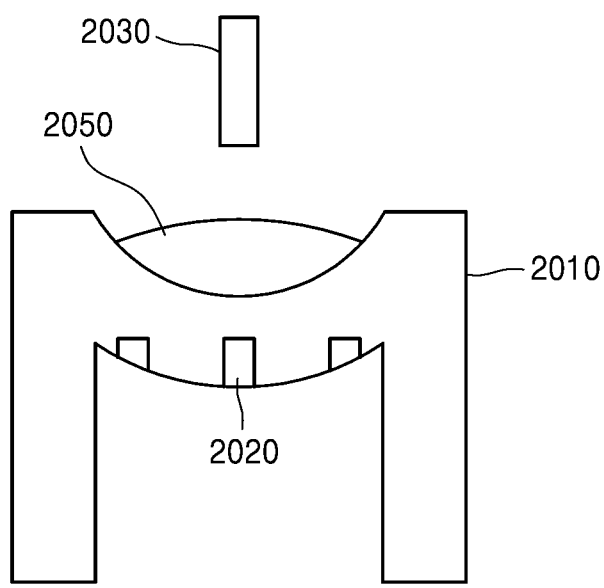

Referring to FIG. 27A, a mould 2010 capable of molding the contact lens is prepared. The mould 2010 according to the present embodiment includes an electromagnet 2020 in a lower portion of the mould 2010 in order to set a reference location. A polymer injector 2030 injects liquid polymer 2050 into the mould 2010.

Figure 27B:
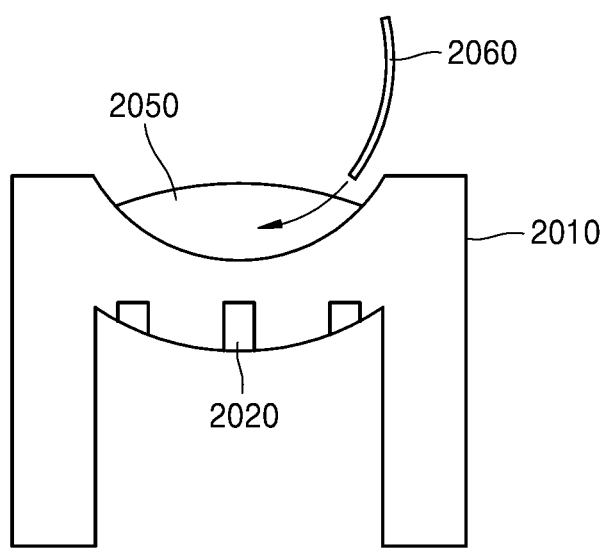

A circuit thin film 2060 including an electronic element unit (for example, 120 of FIG. 1) may be manufactured using a well-known method. As shown in FIG. 27B, the manufactured circuit thin film 2060 is dipped into the liquid polymer 2050, starting from an edge of the manufactured circuit thin film 2060.

Figure 27C:
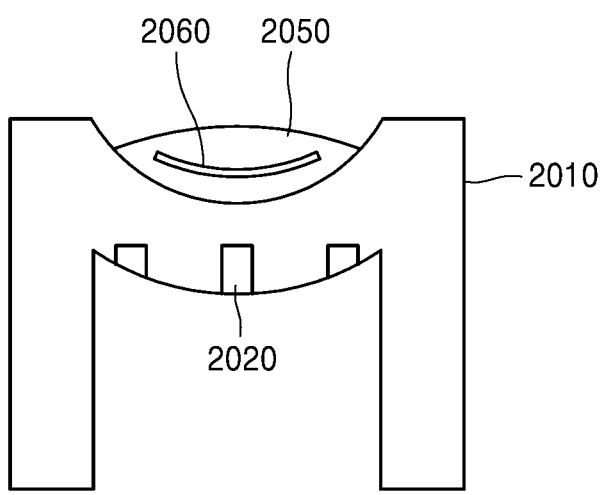

Referring to FIG. 27C, when the circuit thin film 2060 is completely dipped into the liquid polymer 2050, the electromagnet 2020 is driven. The intensity of the electromagnet 2020 is appropriately adjusted such that the circuit thin film 2060 floats on the liquid polymer 2050 due to a surface tension of the liquid polymer 2050 and magnetism of the electromagnet 2020.

Figure 27D:
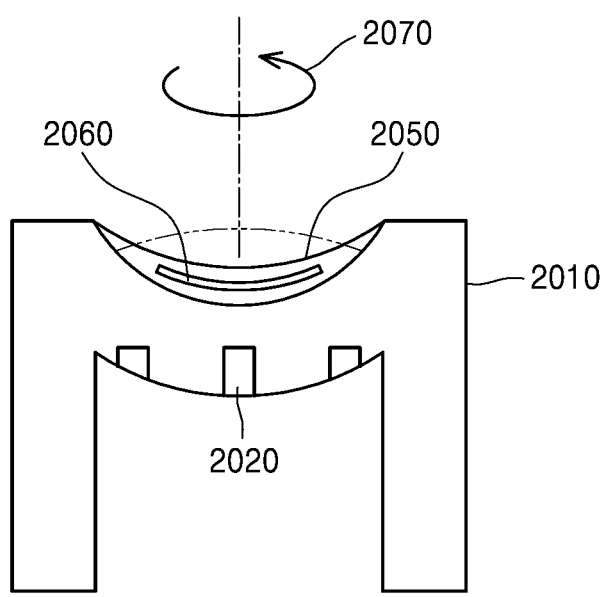
Figure 27E:
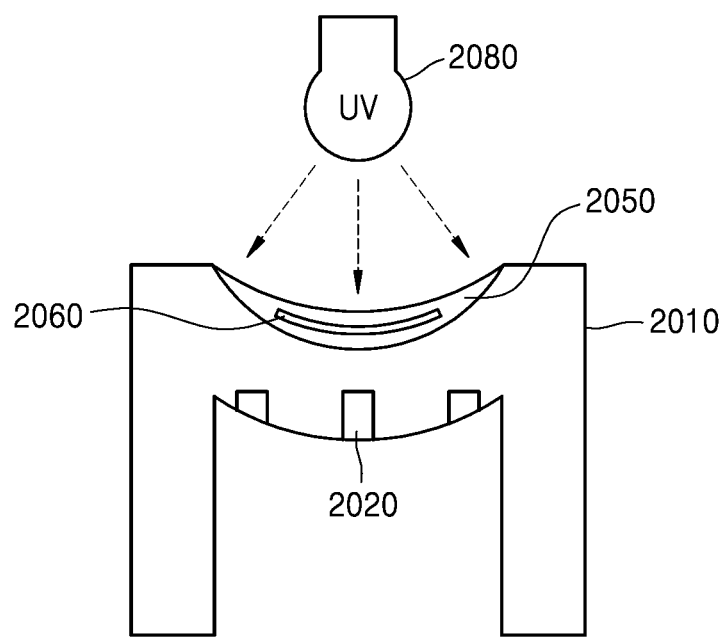

Referring to FIG. 27D, the mould 2010 is rotated such that the liquid polymer 2050 has a predetermined curvature. At this time, to prevent rotation of the circuit thin film 2060 from mismatching with rotation of the polymer 2050 due to a centrifugal force, the intensity of the electromagnet 2020 is adjusted according to a spinning speed. As shown in FIG. 27E, while the mould 2010 is being rotated such that the liquid polymer 2050 has a predetermined curvature, the liquid polymer 2050 is solidified via UV curing.

Figure 27F:
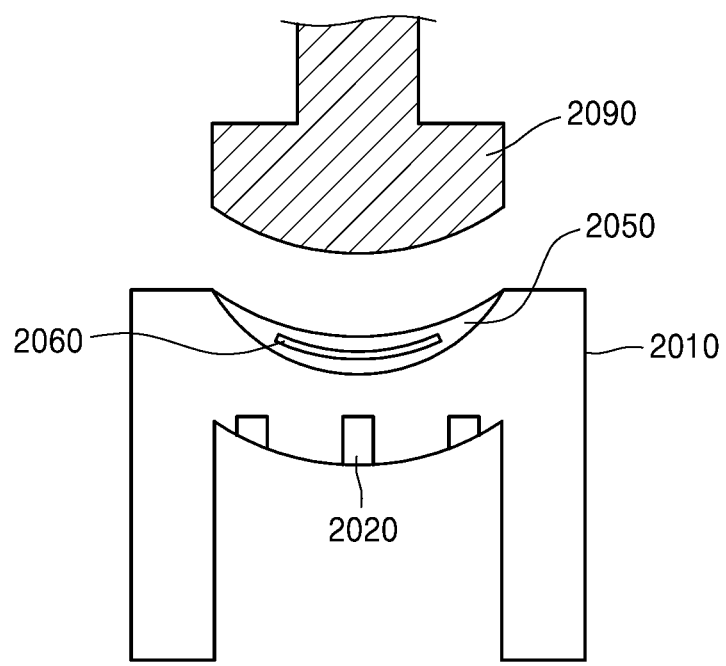

As shown in FIG. 27F, a surface of the hardened polymer 2050 is polished by a polisher 2090, thereby completing the manufacture of the contact lens.

Figure 28A:
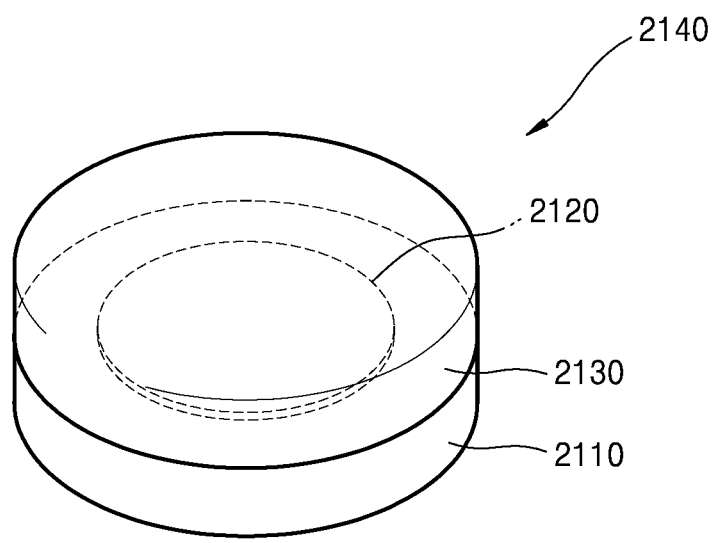
FIGS. 28A and 28B are views for explaining a method of manufacturing a contact lens, according to another embodiment.
Figure 28B:
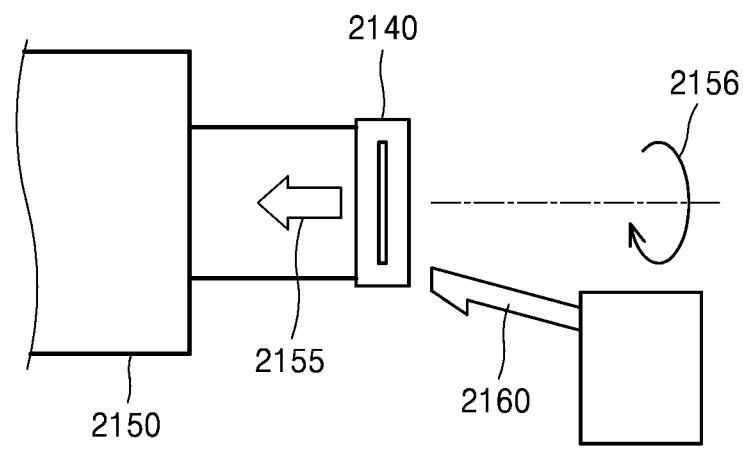

FIGS. 28A and 28B are views for explaining a method of manufacturing a contact lens, according to another embodiment.

Referring to FIG. 28A, a piezoelectric element, and a circuit thin film 2120 including an electronic element unit (for example, 120 of FIG. 1) are independently manufactured using well-known methods. Next, primary polymer 2110 is put into a mould, the circuit thin film 2120 is then put into the mould, and then secondary polymer 2130 is injected, thereby forming a cylindrical button 2140 including the circuit thin film 2120.

Referring to FIG. 28B, a fixer 2150 fixes the button 2140 by using an air pressure 2155, and, in this state, the button 2140 is cut by a cutting machine 2160 under the control of a computer to form a curve of a lens, and the curve of the lens is polished to have a smooth surface.

FIGS. 29A-29D are views for explaining a method of manufacturing a contact lens, according to another embodiment.

Figure 29A:
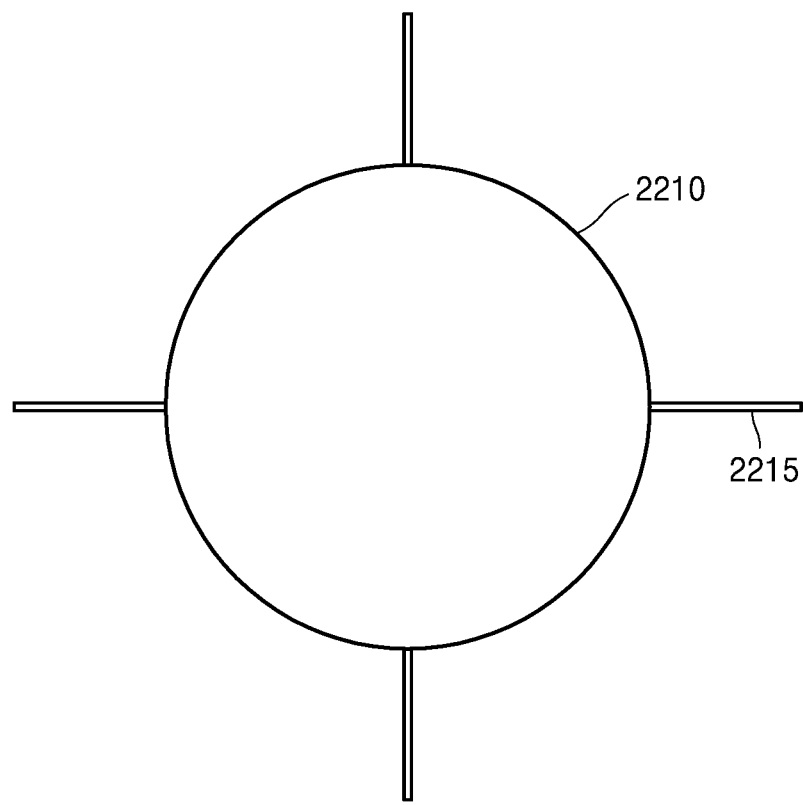
FIGS. 29A-29D are views for explaining a method of manufacturing a contact lens, according to another embodiment.

Referring to FIG. 29A, a piezoelectric element, and a circuit thin film 2210 including an electronic element unit (for example, 120 of FIG. 1) are independently manufactured using well-known methods. A lid line 2215 extends outwards from the circuit thin film 2210.

Figure 29B:
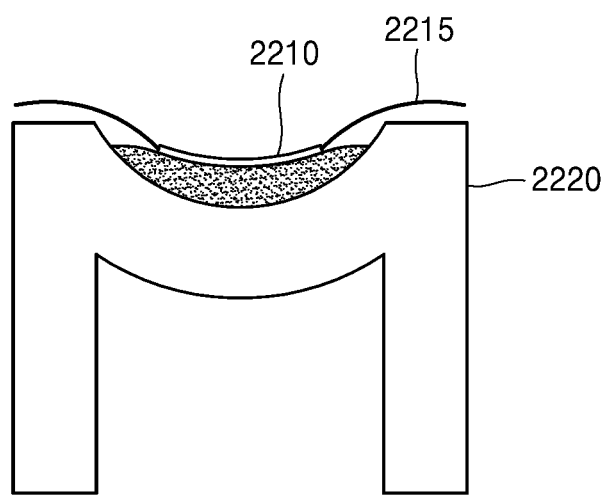

As shown in FIG. 29B, the circuit thin film 2210 is seated on a lower mould 2220, and the lid line 2215 is pulled out of the lower mould 2220 and is connected to a tensioner (not shown). The tensioner is a device for appropriately adjusting a tension of the lid line 2215. The lid line 2215 is adjusted such that the circuit thin film 2210 is fixed at a normal location.

Figure 29C:
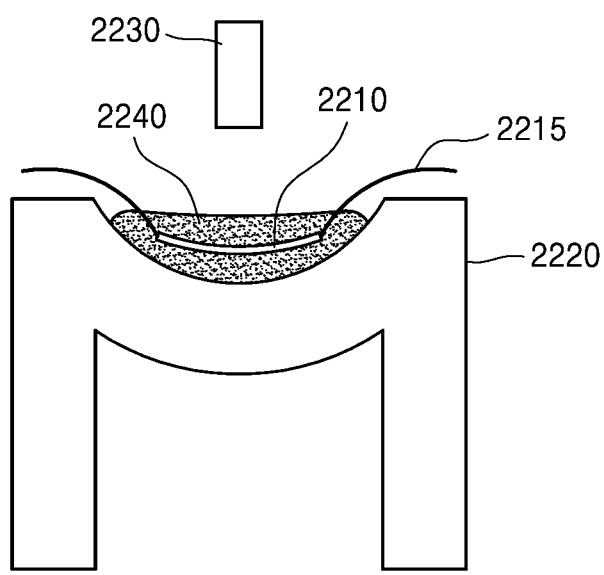

Next, as shown in FIG. 29C, liquid polymer 2240 is injected onto the lower mould 2220 using a moulding machine 2230.

Figure 29D:
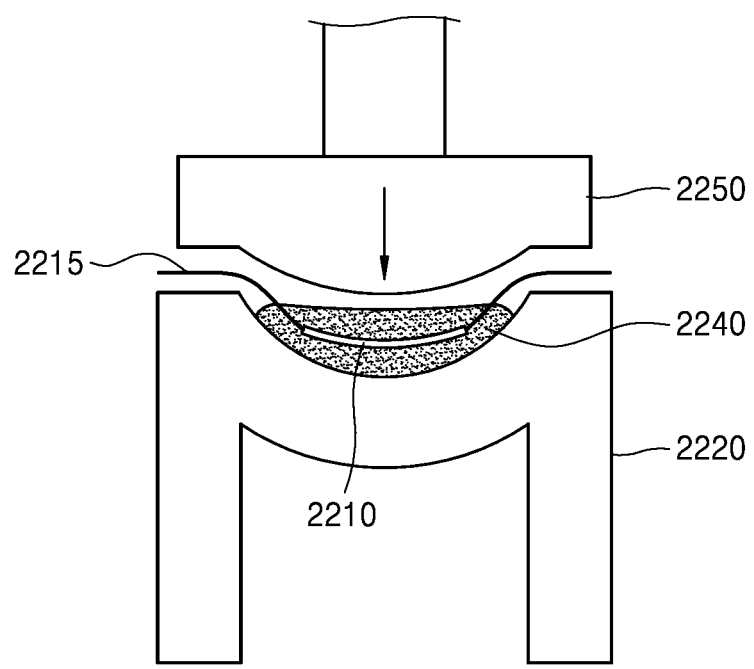

Referring to FIG. 29D, an upper mould 2250 covers the liquid polymer 2240 and accordingly compresses the liquid polymer 2240 within the lower and upper moulds 2220 and 2250, and at the same time pulls the lid line 2215 of a piezoelectric thin film in order to prevent the circuit thin film 2210 from contacting the upper mould 2250 and the lower mould 2220 within a volume created by the lower and upper moulds 2220 and 2250. Thus, the circuit thin film 2210 may float in the liquid polymer.

In the above state, the liquid polymer 2240 is solidified via. UV curing, and then the lid line 2215 is removed by a cutter (not shown) included in the upper mould 2220 or the lower mould 2250 or a pressure at an edge of the upper mould 2220 or the lower mould 2250.

A method of driving the contact lenses according to the above-described embodiments will now be described.

Figure 30:
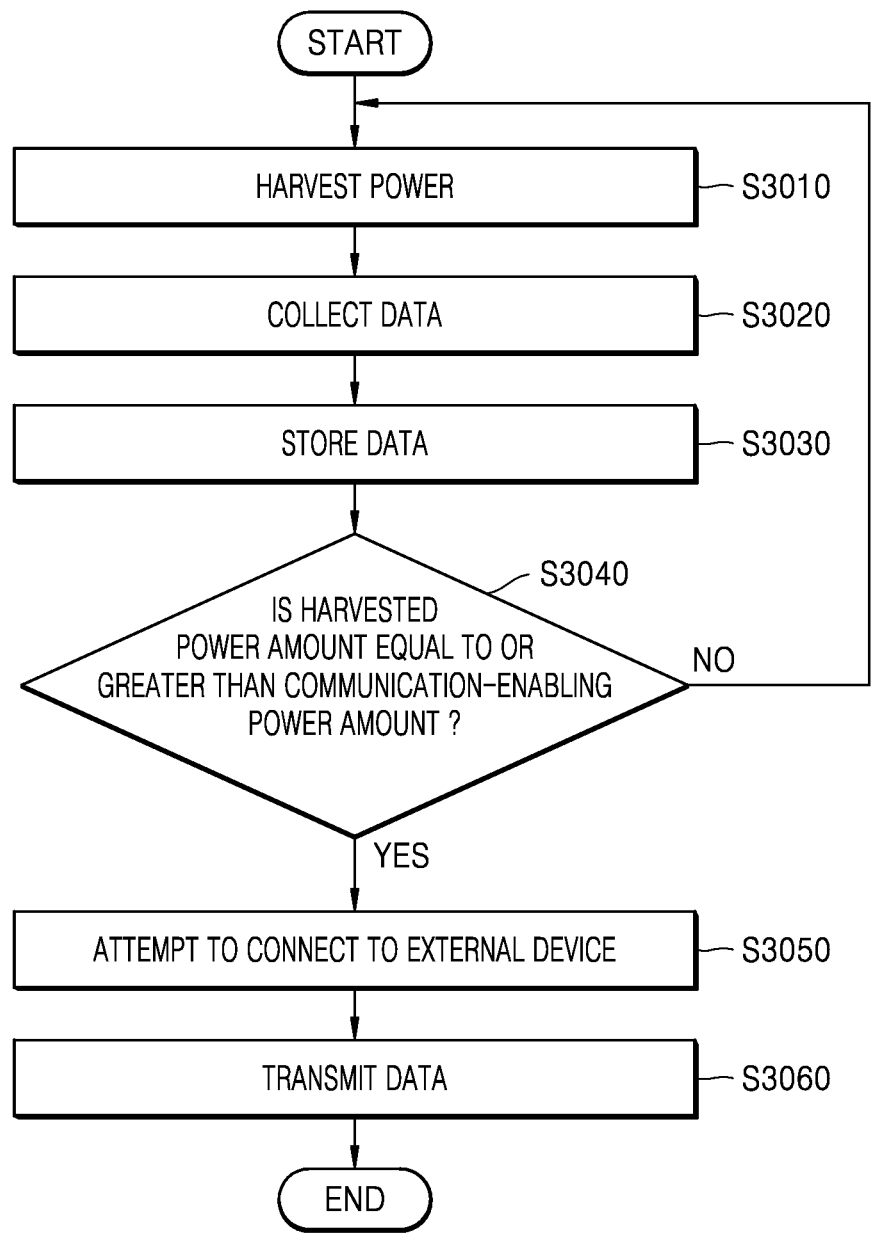
FIG. 30 is a flowchart of a method of driving a contact lens, according to an embodiment.

FIG. 30 is a flowchart of a method of driving a contact lens, according to an embodiment. The contact lens may communicate with an external device while being worn by a user. Referring to FIG. 30, the contact lens harvests a dynamic movement generated by a movement of at least one of the eye and the eyelid of the user as electrical energy, in operation S3010. The electrical energy is produced by an energy harvesting unit (for example, 150 of FIG. 1), and data is collected using the sensor 830 of FIG. 21, in operation S3020, and is stored in the memory 837 of FIG. 21, in operation S3030. Because the eye or the eyelid of a wearer continuously moves, the energy harvesting unit continuously produces the electrical energy in accordance with the movement. In operation S3040, a stored power amount and a communication-enabling power amount are periodically compared with each other. The communication-enabling power amount may denote a power amount required for the contact lens to connect to the external device and transmit at least a one-time amount of data. In operation S3050, when the stored power amount is equal to or greater than the communication-enabling power amount, the contact lens attempts to connect to the external device. In operation S3060, when the contact lens connects to the external device, the content lens transmits data. When the stored power amount is greater than the communication-enabling power amount, the content lens may continuously transmit data. In some cases, as a result of one-time data transmission, the stored power amount may become smaller than the communication-enabling power amount according to consumption of the electrical energy. In this case, until the stored power amount becomes greater than the communication-enabling power amount, the electrical energy may be stored, and then the contact lens may attempt to connect to the external device again. The contact lens may receive a control command from the external device.

Figure 31:
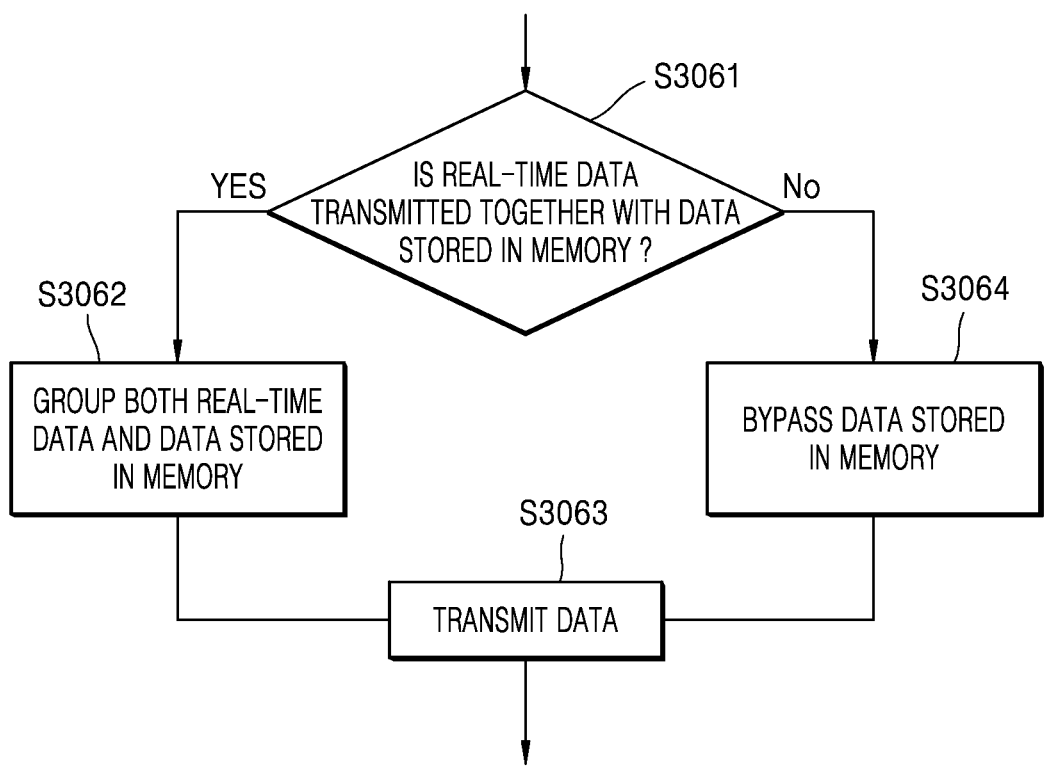
FIG. 31 is a flowchart of an example of data transmission in the flowchart of FIG. 30.

In operation S3060 in which the contact lens transmits data to the external device, the transmitted data may be real-time data detected by a sensor in real time, or may include both the real-time data and data stored in a memory. FIG. 31 is a flowchart of an example of data transmission in the flowchart of FIG. 30. Referring to FIG. 31, the method of driving a contact lens may further include an operation S3061 of determining whether to transmit the real-time data together with the data stored in the memory.

Whether to transmit the real-time data together with the data stored in the memory may be previously stored as a program in the memory. If transmitting the real-time data together with the stored data together is set as a default, a controller may group both the real-time data and the data stored in the memory, in operation S3062, and grouped data may be sequentially transmitted to the external device, in operation S3063. On the other hand, if preferentially transmitting the real-time data is set as a default, the controller bypasses the data stored in the memory, in operation S3064, and may preferentially transmit the real-time data to the external device, in operation S3063. After the transmission of the real-time data to the external device is completed, the data stored in the memory may be transmitted to the external device.

Whether to transmit the real-time data together with the data stored in the memory may depend on a power amount stored in a power storage. If the power amount stored in the power storage is much greater than a minimum amount required to communicate with the external device (i.e., a communication-enabling power amount) or a sufficient amount of electrical energy is produced in real time, the controller may group both the real-time data and the data stored in the memory, in operation S3062, and grouped data may be sequentially transmitted to the external device, in operation S3063. If the power amount stored in the power storage is only the minimum amount required to communicate with the external device (i.e., the communication-enabling power amount), the controller may bypass the data stored in the memory, in operation S3064, and may preferentially transmit the real-time data to the external device, in operation S3063.

Figure 32:
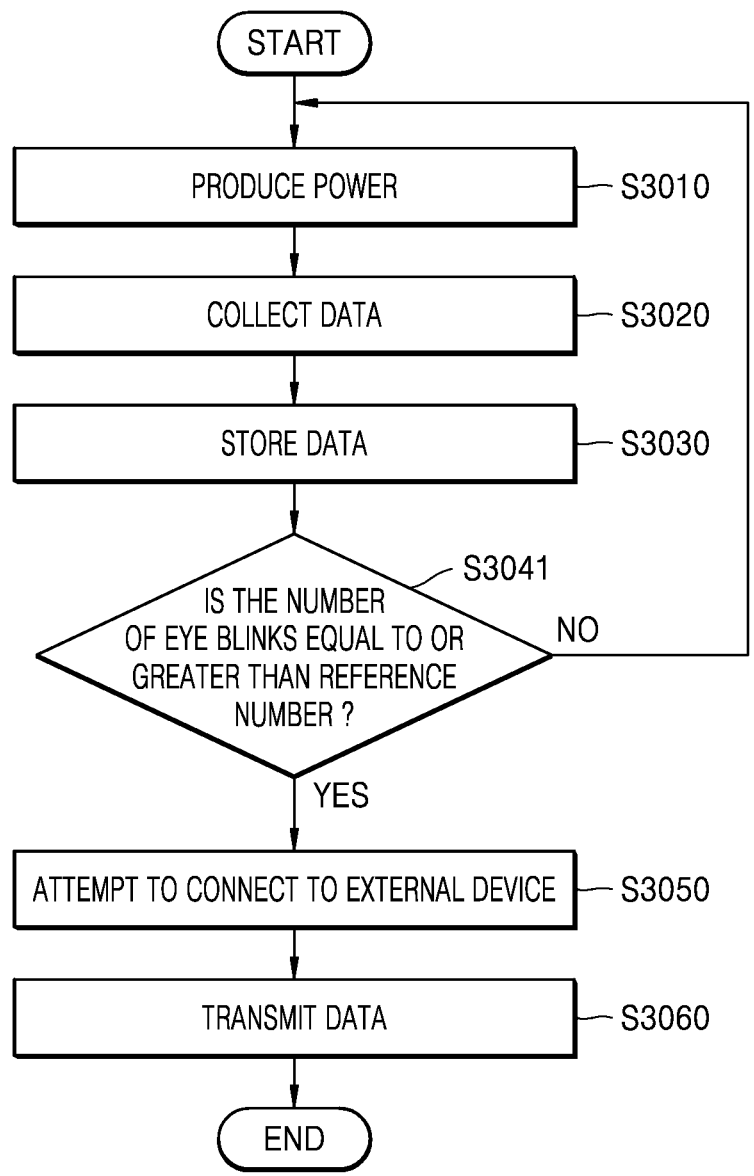
FIG. 32 is a flowchart of a method of driving a contact lens, according to another embodiment.

FIG. 32 is a flowchart of a method of driving a contact lens, according to another embodiment. The contact lens communicates with an external device while being worn by a user. Referring to FIG. 30, the contact lens harvests a dynamic movement generated by a movement of at least one of the eye and the eyelid of the user as electrical energy, in operation S3010. The electrical energy is harvested by an energy harvesting unit (for example, 850 of FIG. 21), and data is collected using the sensor 830 of FIG. 21, in operation S3020, and is stored in the memory 857 of FIG. 21, in operation S3030. Because a power amount is produced in proportion to the number of movements of the eye or eyelid of a wearer, the number of eye blinks necessary for producing a communication-enabling power amount may be previously estimated. Accordingly, it is determined whether the number of eye blinks is greater than a preset reference number, in operation S3041. If the number of eye blinks is greater than the preset reference number, the contact lens connects to the external device, in operation S3050, and transmits data to the external device. As described above, the number of eye blinks is counted based on a voltage waveform of power produced by a piezoelectric element and is stored in a memory. When a sensor includes a photodiode, the number of eye blinks may be counted using the photodiode. Once the contact lens attempts to connect to the external device, the number of eye blinks stored in the memory is reset. In operation S3060 in which the contact lens transmits data to the external device, the transmitted data may be real-time data detected by the sensor in real time, or may include both the real-time data and the data stored in the memory, as described above with reference to FIG. 31.

Figure 33:
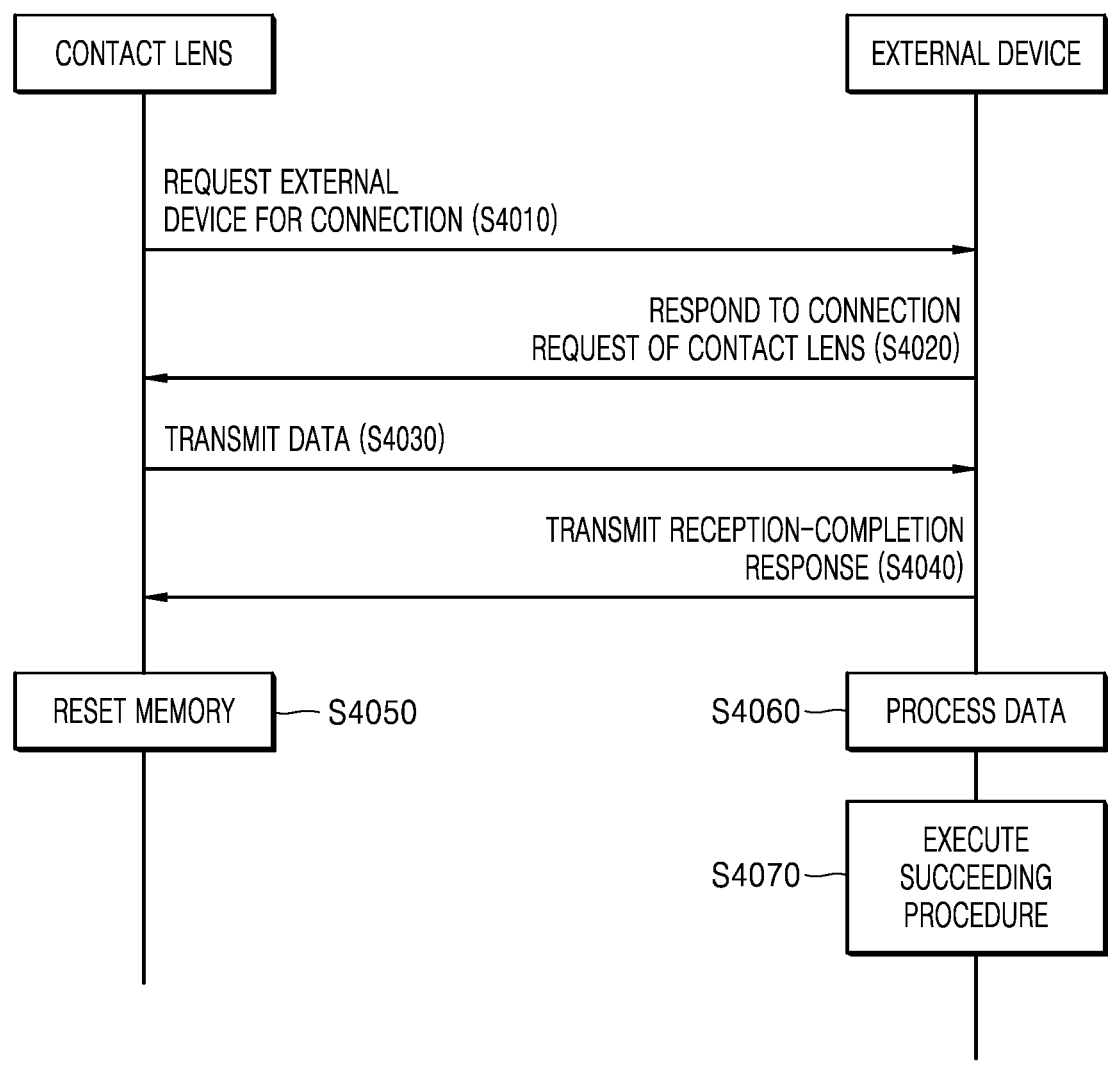
FIG. 33 is a flowchart of a method of operating a system including a contact lens, according to an embodiment.

FIG. 33 is a flowchart of a method of operating a system including a contact lens, according to an embodiment. Referring to FIG. 33, first, the contact lens may request an external device for a connection, in operation S4010. For example, when the stored power amount is greater than the communication-enabling power amount as described above with reference to FIG. 30 or the number of eye blinks is greater than the reference number, the contact lens may first request the external device for a connection while transmitting identification (II)) information of the contact lens to the external device, in operation S4010. The external device may respond to the connection request of the contact lens, in operation S4020, and thus the contact lens and the external device may enter a communication-possible state, namely, may be paired. Next, when the contact lens and the external device are paired, the contact lens transmits data to the external device, in operation S4030. When the external device receives all data, the external device transmits a reception-completion response to the contact lens, in operation S4040. The contact lens resets the memory by removing the data from the memory, in operation S4050. In some cases, the external device may first transmit a data transmission command to the contact lens, and, in response, the contact lens may transmit data to the external device. The external device processes the received data, in operation S4060, and executes a succeeding procedure, in operation S4070. For example, the contact lens may process data measured by itself according to purposes, but a processing procedure that requires a high-level calculation or a high power amount may be processed by the external device. In this situation, the external device may receive data collected by the contact lens in real time or at regular time intervals as described above and may perform a calculation by using the received data. As described above, the contact lens may transmit the collected data in real time or in specific data units. When the contact lens transmits the collected data in specific data units, the contact lens may directly instruct the connected external device to execute a calculation on each data unit. For example, when the contact lens measures blood sugar, the external device stores information about previously-measured blood sugar and compares the information about previously-measured blood sugar with a real-time blood sugar amount, and, when it is determined that real-time blood sugar rapidly changes, the external device may inform the user that blood sugar is high, via a display, a speaker, a vibrator, or the like.

Figure 34:
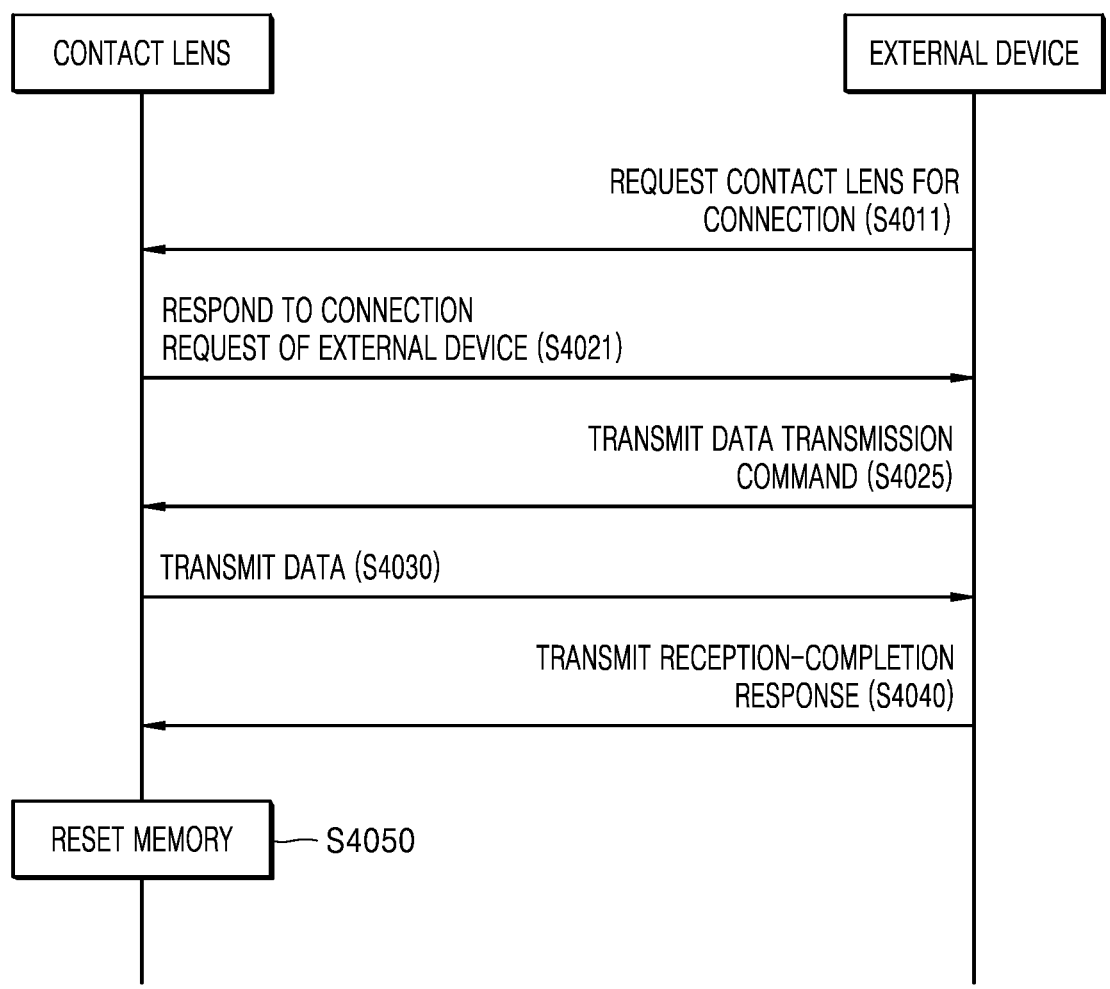
FIG. 34 is a flowchart of a method of operating a system including a contact lens, according to another embodiment.

FIG. 34 is a flowchart of a method of operating a system including a contact lens, according to another embodiment. The present embodiment is not limited to a case where the contact lens communicates with an external device while being worn by a user, and includes a case where the contact lens is taken off from a wearer.

Referring to FIG. 34, first, the external device may request the contact lens for a connection, in operation S4011. For example, the external device may request the contact lens for a connection periodically (for example, every 30 minutes, every one hour, or every day). The contact lens may respond to the connection request of the external device, in operation S4021, and thus the contact lens and the external device may enter a communication-possible state, namely, may be paired. When a power amount stored in the contact lens is smaller than the communication-enabling power amount or connection is not accomplished for any other reason, the external device re-attempts to connect to the contact lens continuously during a predetermine time period (for example, one minute or 10 minutes) or periodically. The contact lens receives a data transmission command to the external device, in operation S4025, and then transmits data. When the external device receives all data, the external device transmits a reception-completion response to the contact lens, in operation S4040. The contact lens resets the memory by removing the data from the memory, in operation S4050.

Figure 35:
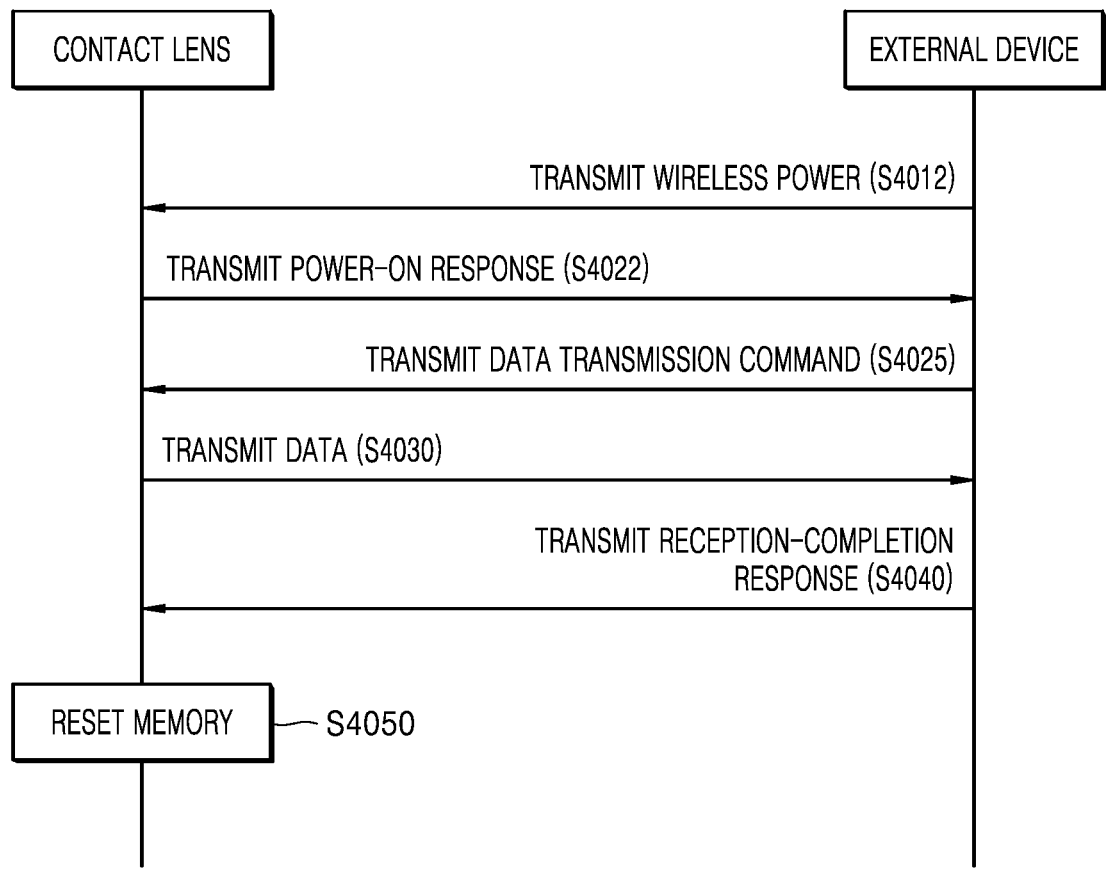
FIG. 35 is a flowchart of a method of operating a system including a contact lens, according to another embodiment.

FIG. 35 is a flowchart of a method of operating a system including a contact lens, according to another embodiment. The present embodiment illustrates a case where the contact lens is taken off from a wearer. Referring to FIG. 35, the contact lens according to the present embodiment further includes a wireless power reception module in addition to an energy harvesting unit, such as a piezoelectric element or a biofuel cell. An external device also further includes a wireless power transmission module. For example, the external device may be a wireless charging pad, the pad may include a transmission antenna having a coil or microstrip shape, and the antenna matches with an antenna (839 of FIG. 21) included in the contact lens.

When the contact lens is placed adjacent to the external device, the external device transmits wireless power to the contact lens according to an electromagnetic induction method or a magnetic resonance method, in operation S4012. Data for communication (for example, time information and a control command) together with a power source may be encoded and then transmitted via transmitted waves, and the contact lens may decode the transmitted waves to separate the power and the data from each other and utilize them. The contact lens receives and stores the transmitted wireless power. When a stored power amount is equal to or greater than the communication-enabling power amount, the contact lens transmits a power-on response to the external device, in operation S4022. When the external device receives the power-on response from the contact lens, the external device transmits a data transmission command to the contact lens, in operation S4025. When the contact lens receives the data transmission command to the external device, in operation S4025, the contact lens transmits data to the external device, in operation S4030. When the external device receives all data, the external device transmits a reception-completion response to the contact lens, in operation S4040. The contact lens resets the memory by removing the data from the memory, in operation S4050.

Figure 36:
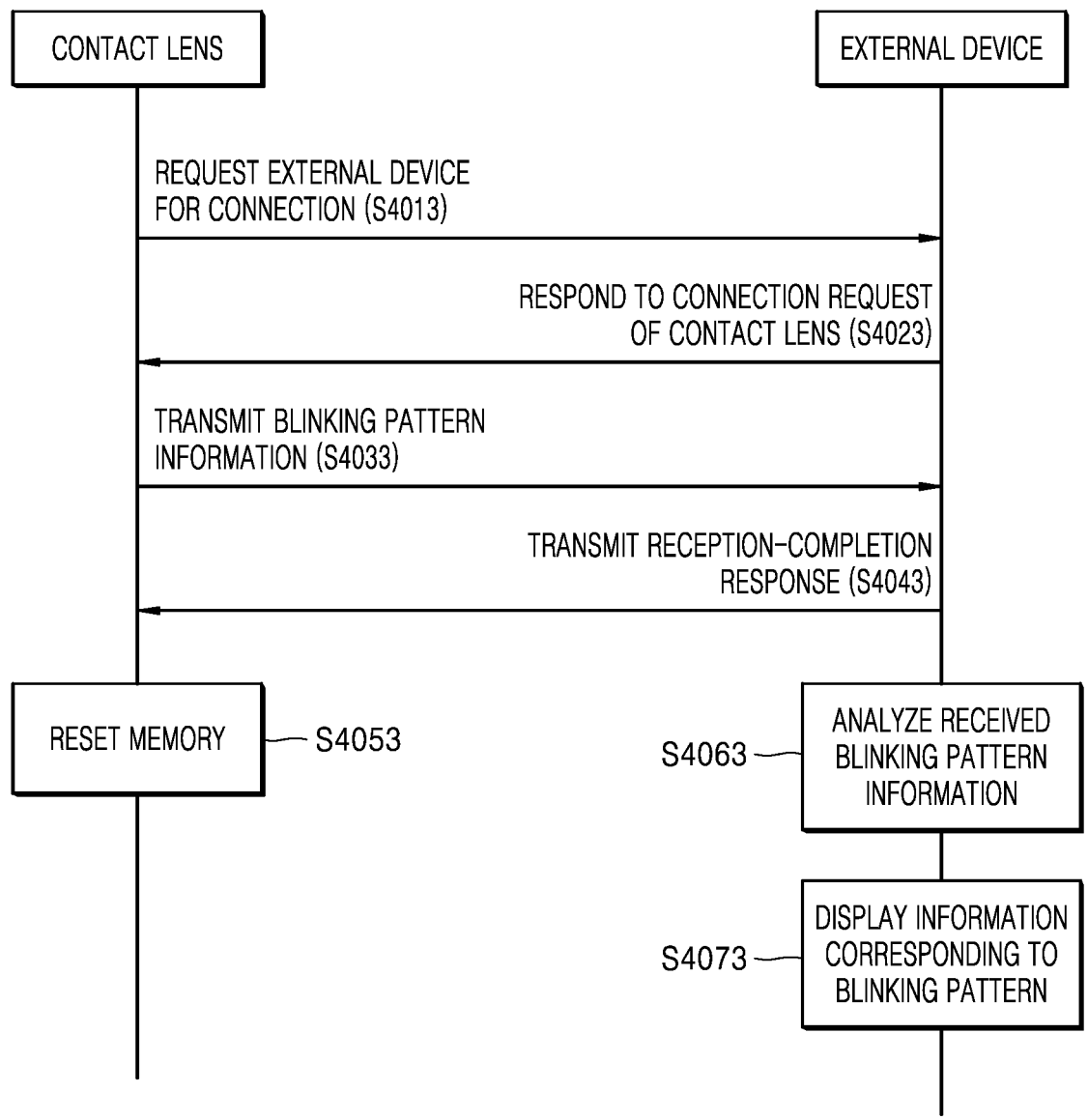
FIG. 36 is a flowchart of a method of operating a system including a contact lens, according to another embodiment.
Figure 37:
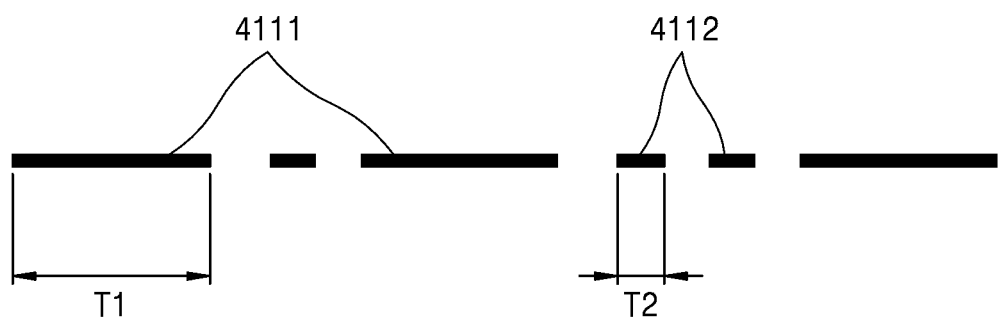
FIG. 37 illustrates an example of a blinking pattern.

FIG. 36 is a flowchart of a method of operating a system including a contact lens, according to another embodiment, and FIG. 37 illustrates an example of a blinking pattern.

Referring to FIG. 36, first, the contact lens may request an external device for a connection, in operation S4013. For example, when the stored power amount is greater than the communication-enabling power amount as described above with reference to FIG. 30 or the number of eye blinks is greater than the reference number, the contact lens may request the external device for a connection while transmitting ID information of the contact lens to the external device. The external device may respond to the connection request of the contact lens, in operation S4023, and thus the contact lens and the external device may enter a communication-possible state, namely, may be paired. Next, when the contact lens and the external device are paired, the contact lens transmits blinking pattern information to the external device, in operation S4033. When the external device receives the blinking pattern information, the external device transmits a reception-completion response to the contact lens, in operation S4043. The contact lens resets the memory by removing the blinking pattern information from the memory, in operation S4053. The external device analyzes the received blinking pattern information, in operation S4053, and displays information corresponding to a blinking pattern, in operation S4073.

A user may intentionally vary a duration of eye-closing and a time interval between eye-closing and eye-closing. For example, the user may blink while distinguishing a case where a duration of eye closing is long from a case where a duration of eye closing is short. Referring to FIG. 37, given that a case T1 when a duration of eye closing is long is referred to as a first eye blink 4111 and a case T2 when a duration of eye closing is short is referred to as a second eye blink 4112, various combinations of the first eye blinks 4111 and the second eye blinks 4112 may contain predetermined information. For example, a blinking pattern (namely, a combination of the first eye blinks 4111 and the second eye blinks 4112) may correspond to a character, such as a Morse code. Matching data of information according to a combination of the first eye blinks 4111 and the second eye blinks 4112 may be previously stored in a memory of the external device. The external device may compare the received blinking pattern information with the matching data to thereby extract information corresponding to the blinking pattern. For example, the user may transmit a predetermined character or sentence to the external device by blinking in a pattern of a combination of the first eye blinks 4111 and the second eye blinks 4112 according to a predetermined table, and the external device may display the predetermined character or sentence included in the blinking pattern. As another example, the blinking pattern may match with a control command of controlling the external device. In this case, the user may control the external device by combining the first eye blinks 4111 with the second eye blinks 4112 and blinking according to the combination.

Figure 38:
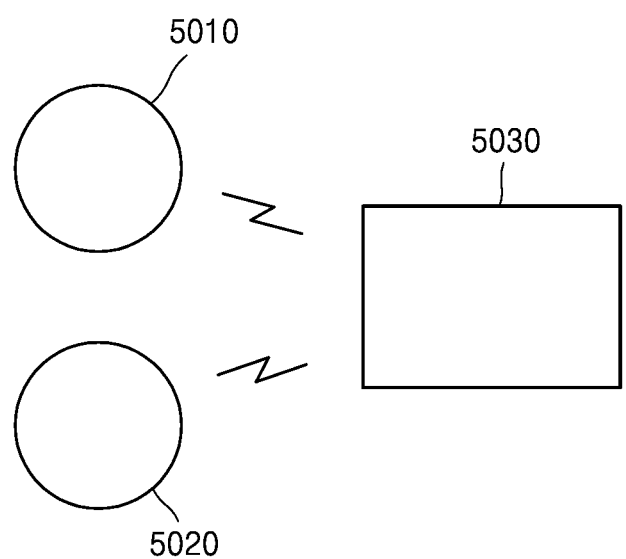
FIG. 38 is a schematic diagram of a system including a contact lens, according to another embodiment.
Figure 39:
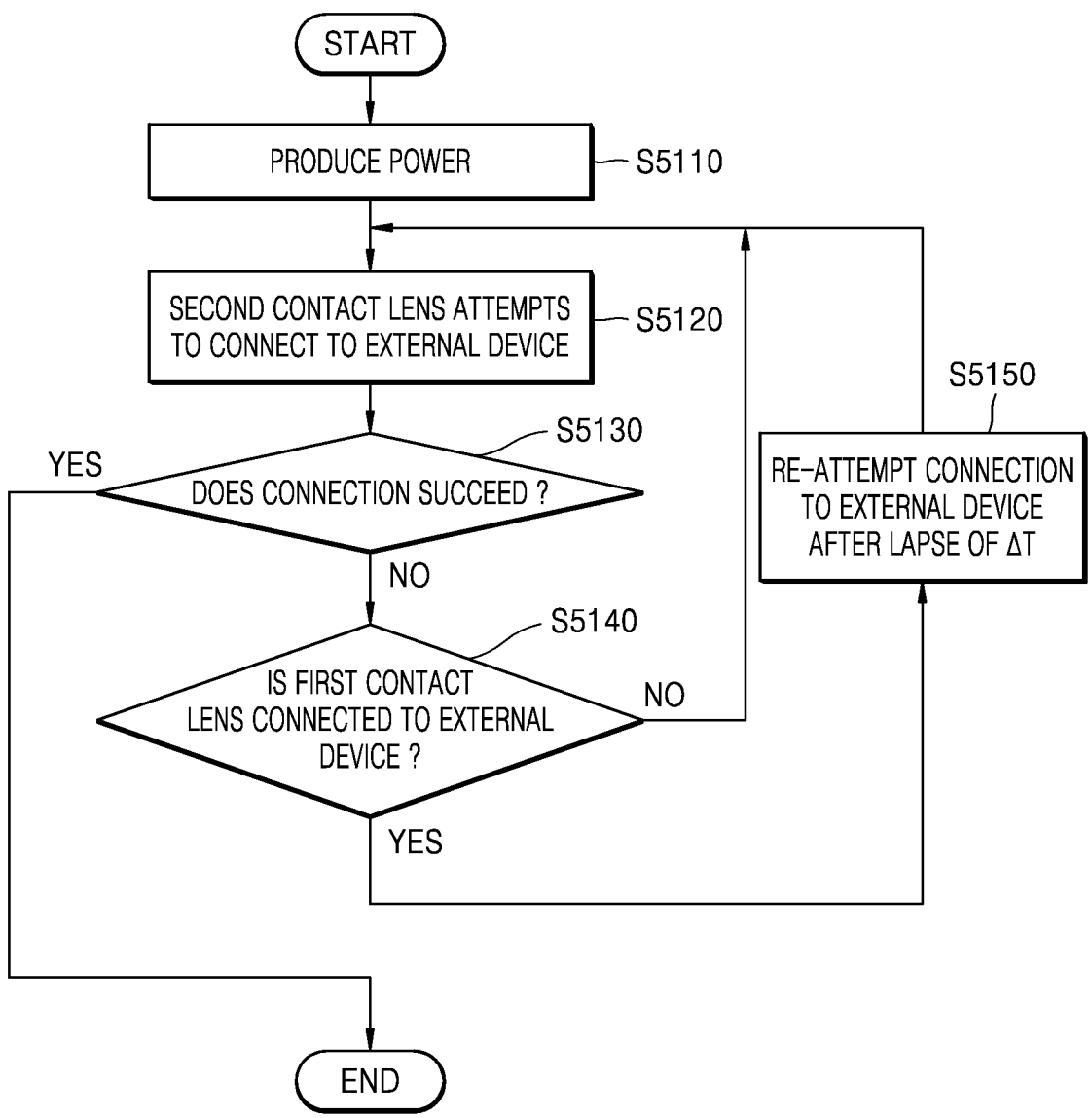
FIG. 39 is a flowchart of a method of operating the system of FIG. 38.

FIG. 38 is a schematic diagram of a system including a contact lens, according to another embodiment, and FIG. 39 is a flowchart of a method of operating the system according to the present embodiment.

Referring to FIGS. 38 and 39, the system according to the present embodiment includes first and second contact lenses 5010 and 5020 respectively worn on both eyes of a wearer, and an external device 5030.

The first contact lens 5010 and the second contact lens 5020 may interoperate with the external device 5030 by using different communication methods and different frequency bands or by using the same communication method and the same frequency band. For example, after the first and second contact lenses 5010 and 5020 are worn on the eyes, stored power amounts of the first and second contact lenses 5010 and 5020 reach the communication-enabling power amount due to a power source charged due to blinking of the eyelids soon after the wearing, in operation S5110. Even when the first and second contact lenses 5010 and 5020 are worn on both eyes simultaneously, one of the first contact lens 5010 and the second contact lens 5020 first reaches the communication-enabling power amount.

The first contact lens 5010 and the second contact lens 5020 may use the same protocol and different frequency bands. In this case, when the first contact lens 5010 and the second contact lens 5020 communicate with the external device 5030 by using different frequency bands even when using the same protocol, each of the first contact lens 5010 and the second contact lens 5020 may communicate with the external device 5030 regardless of which one of the first contact lens 5010 and the second contact lens 5020 first reaches the communication-enabling power amount.

The first contact lens 5010 and the second contact lens 5020 may use the same protocol and the same frequency band. In this case, the first and second contact lenses 5010 and 5020 may generate respective distinguishable IDs within the same frequency. When a contact lens that first reaches the communication-enabling power amount (for example, the first contact lens 5010) is paired with the external device 5030, although the second contact lens 5020 attempts to connect to the external device 5030, in operation S5130, this attempt may fail because of the connection of the first contact lens 5010, in operation S5140. The first and second contact lenses 5010 and 5020 search for other neighboring contact lenses that use the same protocol and the same frequency band as those of the first and second contact lenses 5010 and 5020. However, because the intensity of waves emitted from a contact lens is very weak, only waves in a region close to a length between the eyes may be specified as radiation power of a communication-possible level. Accordingly, when a tick signal for searching is radiated at intervals of non-specific time, another contact lens in an inactive status may receive the tick signal stochastically. In other words, when the first contact lens 5010 is paired with the external device 5030, the second contact lens 5020 may ascertain whether the first contact lens 5010 connects to the external device 5030, from a tick signal and an ID of the first contact lens 5010, in operation S5140. When a connection failure of the second contact lens 5020 is irrelevant to the connection of the first contact lens 5010, the second contact lens 5020 immediately re-attempts to connect to the external device 5030. If the connection failure of the second contact lens 5020 is due to the connection of the first contact lens 5010 with the external device, a communication frequency may be set to be activated based on different time intervals with respect to a time axis within the same frequency channel in order to prevent frequency confusion, in operation S5150. For example, the second contact lens 5020 may re-attempt a connection to the external device after the lapse of Δt. Herein, Δt is smaller than a time cycle in which the first and second contact lenses 5010 and 5020 connect to the external device. For example, Δt may be ½, ⅓, ¼, or the like of the time cycle in which the first and second contact lenses 5010 and 5020 connect to the external device. The first and second contact lenses 5010 and 5020 individually produce protocols capable of transmitting their own information as described above, and then exchange data with the external device 5030 so that the external device 5030 may process the data. The subject of the processing may be the external device 5030 (for example, a mobile phone, a TV, or any other wearable device) directly interoperating with the first and second contact lenses 5010 and 5020. Alternatively, when the external device 5030 directly interoperating with the first and second contact lenses 5010 and 5020 is connected to a network, the external device 5030 may transmit data received from the first and second contact lenses 5010 and 5020 by using the resources of the network to a second external device (e.g., a server, a computer processing device, or a recording device) via the network so that the second external device may process the data or store the data separately. This system structure may be dynamically and variably applied according to network circumstances. The external device 5030 may receive pieces of data from the first and second contact lenses 5010 and 5020 and process the received pieces of data according to respective processors/threads. The external device 5030 may transmit results of the processing to the first and second contact lenses 5010 and 5020 or respond to the first and second contact lenses 5010 and 5020 after the processing, in separate forms that conform to tick signals or protocols of waves individually sent by the first and second contact lenses 5010 and 5020. If a communication connection is unpredictably terminated due to an unstable power environment of the first and second contact lenses 5010 and 5020, after information about a previously-connected profile is deleted, the external device 5030 may newly attempt to communicate with a communication-terminated contact lens. In this case, the external device 5030 may avoid a frequency channel used by the communication-terminated contact lens in order to avoid interference with a contact lens with which a connection is not terminated. A contact lens having newly entered in an initial state after communication is terminated may attempt to connect to the external device 5030. At this time, the contact lens may detect an activation state of a channel transmitted by a contact lens of which connection is not terminated, consider a starting point of the activation state as a tick, and avoid the channel or adjusting a time interval in the channel to thereby re-connect to the external device 5030.

The first contact lens 5010 and the second contact lens 5020 may provide the same function and complement the provided function. For example, when sensors of the first and second contact lenses 5010 and 5020 collect and measure the components of tear, the external device 5030 may estimate measurement values respectively measured by the first and second contact lenses 5010 and 5020 and correct a final component content of a specific component. Thus, when measuring a bio activity sign, the external device 5030 may sum and operate measurement values respectively measured by the first and second contact lenses 5010 and 5020 to thereby improve reliability of the measured bio activity sign. For example, the measurement values respectively measured by the first and second contact lenses 5010 and 5020 may be temperatures, pulses, or the like.

The first contact lens 5010 and the second contact lens 5020 may include different types of sensors and may complement each other or simultaneously perform different functions, thereby smoothly tracking a specific biomarker or a situation of the wearer. For example, the first contact lens 5010 may include a sensor that provides a function of measuring and tracking a content of a lipid (fat component) included in tear from one eye, and the second contact lens 5020 may include a sensor that provides a function of measuring the number of eyelid blinks from the other eye. In this case, the first and second contact lenses 5010 and 5020 may track a variation in the lipid component included in tear according to eyelid blinks within a specific time period, thereby the external device 5030 may estimate an influence of the variation in the lipid component according to the number of eyelid blinks upon a dry eye syndrome. Accordingly, when the number of eyelid blinks does not reach a reference value or excessive moisture evaporation of the eye surface is expected due to a too small lipid component, this may be informed to the wearer via another external device capable of communicating with the external device 5030. When the first contact lens 5010 and/or the second contact lens 5020 includes the display 835 of FIG. 21, such as light-emitting devices, the display 135 may display an event regarding a specific condition to the wearer. When the wearer displays an event, the first contact lens 5010 and the second contact lens 5020 may communicate with each other such that one or both thereof may display an event, and thus the wearer may recognize the event. Alternatively, after measured data transmitted to the external device 5030 interoperating with the first contact lens 5010 and/or the second contact lens 5020 is analyzed by the external device 5030, the external device 5030 may instruct the first contact lens 5010 and/or the second contact lens 5020 to generate an event and display the event.

As another example, the first contact lens 5010 may include a sensor capable of performing a function of tracking a movement of one eye, and the second contact lens 5020 may include a logic capable of performing a function of tracking the number of eye blinks of the other eye. Accordingly, the first and second contact lenses 5010 and 5020 may track both the eye movement of the wearer and the number of eye blinks. Because the eye movement and the blinking may be combined variously, the first and second contact lenses 5010 and 5020 may detect a combination of an eye movement and blinking of the wearer and thus detect a command intended by the wearer to thereby instruct the external device 5030 to perform this command. The eye movement and the blinking may be detected by the first and second contact lenses 5010 and 5020 are an example of distinguished measurement aspects, but the present invention is not limited thereto. When the first and second contact lenses 5010 and 5020 detect at least two different measurement aspects from the wearer and transmit information about the at least two different measurement aspects to the external device 5030, the external device 5030 may match a combination of the at least two different measurement aspects with a predetermined command table and perform a command corresponding to the combination. In other words, by detecting a combination of the at least two different measurement aspects from the wearer, the first and second contact lenses 5010 and 5020 may instruct the external device 5030 to perform a command intended by the wearer.

Although a contact lens including an energy harvesting unit according to the present invention has been described with reference to the embodiments illustrated in the drawings in order to facilitate understanding of the present invention, the illustrated embodiments are only examples, and various modifications to the illustrated embodiments and other equivalent embodiments may be possible. Therefore, the scope of the present invention should be determined by the accompanying claims.

The invention claimed is:

1. A contact lens comprising:
   a lens portion placed on an eye of a user;
   a sensor configured to detect biometric information of the user;
   an energy harvesting device configured to transform a dynamic movement generated by a movement of an eye part of the user into electrical energy and provide the sensor with the electrical energy;
   a display configured to output information detected by the sensor or information received from an external electronic device; and
   a spacer, positioned parallel to an optical axis between the lens portion and the energy harvesting device, configured to reduce transmission of a stress generated according to the movement of the eye part to a back side of the lens portion or the energy harvesting device,
   wherein the display is embedded in the lens portion that is placed on the eye of the user, and
   wherein the spacer, positioned parallel to an optical axis between the lens portion and the energy harvesting device, includes at least one of an air layer or a liquid layer.

2. The contact lens of claim 1, wherein, when an electrical energy amount harvested by the energy harvesting device is equal to or greater than a sensing-enabling power amount, the sensor is driven to detect information of the user.

3. The contact lens of claim 1, further comprising:
   a communicator configured to transmit information detected by the sensor to an external device; and at least one processor configured to control the sensor and the communicator.

4. The contact lens of claim 3, wherein, when an electrical energy amount harvested by the energy harvesting device is equal to or greater than a communication-enabling power amount, the at least one processor drives the communicator to attempt to connect to the external device.

5. The contact lens of claim 3, wherein, when a number of eye blinks of the user is equal to or greater than a reference number, the at least one processor drives the communicator to attempt to connect to the external device.

6. The contact lens of claim 3, wherein the information detected by the sensor is at least one of a number of eye blinks of the user, a duration of eye-closing of the user, a pattern of blinking of the user, an eyeball movement of the user, or information about a biomaterial included in tear of the user.

7. The contact lens of claim 1, wherein the energy harvesting device comprises a first piezoelectric element, the first piezoelectric element comprising a first piezoelectric layer that is bent due to the movement of the eye part of the user, and first and second electrodes that contact the first piezoelectric layer and collect electrical energy generated due to deformation of the first piezoelectric layer.

8. The contact lens of claim 7, wherein the first and second electrodes are arranged apart from each other on a first surface of the first piezoelectric layer.

9. The contact lens of claim 7, wherein the first and second electrodes are respectively arranged on a first surface of the first piezoelectric layer and a second surface of the first piezoelectric layer opposite to the first surface.

10. The contact lens of claim 7, wherein the energy harvesting device further comprises a second piezoelectric element, the second piezoelectric element comprising a second piezoelectric layer and third and fourth electrodes that contact the second piezoelectric layer and collect electricity generated due to deformation of the second piezoelectric layer.

11. The contact lens of claim 7, wherein a layer equipped with the sensor and a layer equipped with the first piezoelectric element are different from each other.

12. The contact lens of claim 7, wherein the first piezoelectric element is provided on a center region of the lens portion, and the sensor is provided on an outer region of the lens portion.

13. The contact lens of claim 1, wherein the energy harvesting device further comprises a power storage device.

14. The contact lens of claim 13, wherein the energy harvesting device storage device comprises a capacitor.

15. The contact lens of claim 14, wherein the capacitor is provided on an outer circumference of the lens portion.

16. The contact lens of claim 8, wherein the first and second electrodes face each other and are arranged such as to elongate toward each other at a plurality of spots and alternate with each other.

17. The contact lens of claim 9, wherein each of the first and second electrodes is formed in a lattice pattern, a zigzag pattern, or a comb electrode pattern.

18. The contact lens of claim 7, wherein the sensor and the first piezoelectric element are provided on the same layer.

* * * * *